(12) United States Patent
Thommen et al.

(10) Patent No.: US 10,869,659 B2
(45) Date of Patent: Dec. 22, 2020

(54) SURGICAL INSTRUMENT CONNECTORS AND RELATED METHODS

(71) Applicant: Medos International Sarl, Le Locle (CH)

(72) Inventors: Daniel Thommen, Liestal (CH); Eric Buehlmann, Duxbury, MA (US); Joern Richter, Kandern (DE); Peter Senn, Waldenburg (CH); Veronique Christine Zollmann, Gebenstorf (CH); Thomas Gamache, Westport, MA (US); William Kane, Newport Beach, CA (US); Joseph Amaral, Cumberland, RI (US); John Pracyk, Cumberland, RI (US); Bill Horton, Duxbury, MA (US); John Wright, Dedham, MA (US)

(73) Assignee: Medos International Sarl, Le Locle (CH)

( * ) Notice: Subject to any disclaimer, the term of this patent is extended or adjusted under 35 U.S.C. 154(b) by 67 days.

(21) Appl. No.: 15/786,923

(22) Filed: Oct. 18, 2017

(65) Prior Publication Data

US 2018/0110506 A1     Apr. 26, 2018

Related U.S. Application Data

(63) Continuation-in-part of application No. 15/437,792, filed on Feb. 21, 2017, which is a continuation-in-part of application No. 15/254,877, filed on Sep. 1, 2016.
(Continued)

(51) Int. Cl.
*A61B 17/02* (2006.01)
*A61B 90/00* (2016.01)
(Continued)

(52) U.S. Cl.
CPC ........ *A61B 17/025* (2013.01); *A61B 1/00045* (2013.01); *A61B 1/00091* (2013.01);
(Continued)

(58) Field of Classification Search
CPC ..... A61B 17/02; A61B 17/0293; A61B 17/60; A61B 90/57; A61B 1/32
See application file for complete search history.

(56) References Cited

U.S. PATENT DOCUMENTS

| 4,318,401 A | 3/1982 | Zimmerman |
| 4,573,448 A | 3/1986 | Kambin |

(Continued)

FOREIGN PATENT DOCUMENTS

| CN | 102727309 B | 11/2014 |
| DE | 94 15 039 U1 | 11/1994 |

(Continued)

OTHER PUBLICATIONS

International Search Report for Application No. PCT/IB18/57367, dated Jan. 29, 2019, (4 pages).
(Continued)

*Primary Examiner* — Christopher J Beccia
(74) *Attorney, Agent, or Firm* — Nutter McClennen & Fish LLP

(57) ABSTRACT

Connectors for connecting or linking one instrument or object to one or more other instruments or objects are disclosed herein. In some embodiments, a connector can include a first arm with a first attachment feature for attaching to a first object, such as a surgical access device, and a second arm with a second attachment feature for attaching to a second object, such as a support. The connector can have an unlocked state, in which the position and orientation of the access device can be adjusted relative to the support, and a locked state in which movement of the access device
(Continued)

relative to the support is prevented or limited. Locking the connector can also be effective to clamp or otherwise attach the connector to the access device and the support, or said attachment can be independent of the locking of the connector.

34 Claims, 21 Drawing Sheets

Related U.S. Application Data

(60) Provisional application No. 62/214,297, filed on Sep. 4, 2015, provisional application No. 62/468,475, filed on Mar. 8, 2017.

(51) Int. Cl.

| | | |
|---|---|---|
| *A61B 90/50* | (2016.01) | |
| *A61B 90/57* | (2016.01) | |
| *A61B 1/00* | (2006.01) | |
| *A61B 1/012* | (2006.01) | |
| *A61B 1/018* | (2006.01) | |
| *A61B 1/05* | (2006.01) | |
| *A61B 1/055* | (2006.01) | |
| *A61B 1/07* | (2006.01) | |
| *A61B 1/12* | (2006.01) | |
| *A61B 1/233* | (2006.01) | |
| *A61B 1/267* | (2006.01) | |
| *A61B 1/313* | (2006.01) | |
| *A61B 1/317* | (2006.01) | |
| *A61B 1/32* | (2006.01) | |
| *A61B 5/04* | (2006.01) | |
| *A61B 5/06* | (2006.01) | |
| *A61B 5/00* | (2006.01) | |
| *A61B 17/00* | (2006.01) | |
| *A61B 17/32* | (2006.01) | |
| *A61B 17/34* | (2006.01) | |
| *A61B 17/60* | (2006.01) | |
| *A61B 17/70* | (2006.01) | |
| *A61B 18/18* | (2006.01) | |
| *A61F 2/44* | (2006.01) | |
| *A61F 2/46* | (2006.01) | |
| *A61B 34/20* | (2016.01) | |
| *A61B 34/00* | (2016.01) | |
| *A61B 90/30* | (2016.01) | |
| *A61B 17/16* | (2006.01) | |
| *A61B 17/17* | (2006.01) | |
| *A61B 17/56* | (2006.01) | |
| *A61B 18/00* | (2006.01) | |

(52) U.S. Cl.
CPC ...... *A61B 1/00096* (2013.01); *A61B 1/00103* (2013.01); *A61B 1/00128* (2013.01); *A61B 1/00133* (2013.01); *A61B 1/00135* (2013.01); *A61B 1/00154* (2013.01); *A61B 1/012* (2013.01); *A61B 1/018* (2013.01); *A61B 1/05* (2013.01); *A61B 1/051* (2013.01); *A61B 1/055* (2013.01); *A61B 1/07* (2013.01); *A61B 1/126* (2013.01); *A61B 1/233* (2013.01); *A61B 1/2676* (2013.01); *A61B 1/317* (2013.01); *A61B 1/3132* (2013.01); *A61B 1/3135* (2013.01); *A61B 1/32* (2013.01); *A61B 5/04001* (2013.01); *A61B 5/068* (2013.01); *A61B 5/407* (2013.01); *A61B 5/4041* (2013.01); *A61B 17/00234* (2013.01); *A61B 17/0218* (2013.01); *A61B 17/0293* (2013.01); *A61B 17/320068* (2013.01); *A61B 17/3421* (2013.01); *A61B 17/3423* (2013.01); *A61B 17/3462* (2013.01); *A61B 17/60* (2013.01); *A61B 17/708* (2013.01); *A61B 17/7032* (2013.01); *A61B 17/7074* (2013.01); *A61B 18/1815* (2013.01); *A61B 90/03* (2016.02); *A61B 90/361* (2016.02); *A61B 90/50* (2016.02); *A61B 90/57* (2016.02); *A61F 2/4455* (2013.01); *A61F 2/4611* (2013.01); *A61B 1/00149* (2013.01); *A61B 17/0206* (2013.01); *A61B 17/1637* (2013.01); *A61B 17/1671* (2013.01); *A61B 17/1757* (2013.01); *A61B 17/3439* (2013.01); *A61B 17/70* (2013.01); *A61B 17/7083* (2013.01); *A61B 34/70* (2016.02); *A61B 90/30* (2016.02); *A61B 2017/0034* (2013.01); *A61B 2017/00261* (2013.01); *A61B 2017/00314* (2013.01); *A61B 2017/00345* (2013.01); *A61B 2017/00407* (2013.01); *A61B 2017/00477* (2013.01); *A61B 2017/00557* (2013.01); *A61B 2017/00738* (2013.01); *A61B 2017/00831* (2013.01); *A61B 2017/00858* (2013.01); *A61B 2017/00871* (2013.01); *A61B 2017/00946* (2013.01); *A61B 2017/00991* (2013.01); *A61B 2017/0256* (2013.01); *A61B 2017/0262* (2013.01); *A61B 2017/320075* (2017.08); *A61B 2017/3443* (2013.01); *A61B 2017/3445* (2013.01); *A61B 2017/3447* (2013.01); *A61B 2017/3454* (2013.01); *A61B 2017/3484* (2013.01); *A61B 2017/564* (2013.01); *A61B 2018/00339* (2013.01); *A61B 2018/00565* (2013.01); *A61B 2018/00577* (2013.01); *A61B 2018/1861* (2013.01); *A61B 2018/1869* (2013.01); *A61B 2034/2055* (2016.02); *A61B 2090/034* (2016.02); *A61B 2090/036* (2016.02); *A61B 2090/08021* (2016.02); *A61B 2090/3983* (2016.02); *A61F 2002/4635* (2013.01)

(56) References Cited

U.S. PATENT DOCUMENTS

| | | |
|---|---|---|
| 4,646,738 A | 3/1987 | Trott |
| 4,678,459 A | 7/1987 | Onik et al. |
| 4,863,430 A | 9/1989 | Klyce et al. |
| 4,874,375 A | 10/1989 | Ellison |
| 4,888,146 A | 12/1989 | Dandeneau |
| 5,080,662 A | 1/1992 | Paul |
| 5,195,541 A | 3/1993 | Obenchain |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,615,690 A | 4/1997 | Giurtino et al. |
| 5,618,293 A | 4/1997 | Sample et al. |
| 5,662,300 A | 9/1997 | Michelson |
| 5,688,222 A | 11/1997 | Hluchy et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,792,044 A | 8/1998 | Foley et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey, Jr. et al. |
| 5,954,635 A | 9/1999 | Foley et al. |
| 5,976,075 A | 11/1999 | Beane et al. |
| 6,017,333 A | 1/2000 | Bailey |

(56) References Cited

U.S. PATENT DOCUMENTS

| | | |
|---|---|---|
| 6,053,907 A | 4/2000 | Zirps |
| 6,063,021 A | 5/2000 | Hossain et al. |
| 6,110,182 A | 8/2000 | Mowlai-Ashtiani |
| 6,200,322 B1 | 3/2001 | Branch et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,520,495 B1* | 2/2003 | La Mendola ............ B25B 5/006 24/300 |
| 6,558,407 B1 | 5/2003 | Ivanko et al. |
| 6,575,899 B1 | 6/2003 | Foley et al. |
| 6,579,281 B2 | 6/2003 | Palmer et al. |
| 6,626,830 B1 | 9/2003 | Califiore et al. |
| 6,648,915 B2 | 11/2003 | Sazy |
| 6,676,597 B2 | 1/2004 | Guenst et al. |
| 6,685,724 B1 | 2/2004 | Haluck |
| 6,688,564 B2 | 2/2004 | Salvermoser et al. |
| 6,758,809 B2 | 7/2004 | Briscoe et al. |
| 6,808,505 B2 | 10/2004 | Kadan |
| 6,887,198 B2* | 5/2005 | Phillips ................ A61B 17/02 600/227 |
| 6,983,930 B1 | 1/2006 | La Mendola et al. |
| 7,087,058 B2 | 8/2006 | Cragg |
| 7,104,986 B2 | 9/2006 | Hovda et al. |
| 7,137,949 B2 | 11/2006 | Scirica et al. |
| 7,179,261 B2 | 2/2007 | Sicvol et al. |
| 7,182,731 B2 | 2/2007 | Nguyen et al. |
| 7,226,413 B2 | 6/2007 | McKinley |
| 7,341,556 B2 | 3/2008 | Shalman |
| 7,434,325 B2 | 10/2008 | Foley et al. |
| 7,491,168 B2 | 2/2009 | Raymond et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,771,384 B2 | 8/2010 | Ravo |
| 7,794,456 B2 | 9/2010 | Sharps et al. |
| 7,811,303 B2 | 10/2010 | Fallin et al. |
| 7,931,579 B2 | 4/2011 | Bertolero et al. |
| 7,946,981 B1 | 5/2011 | Cubb |
| 7,951,141 B2 | 5/2011 | Sharps et al. |
| 7,959,564 B2 | 6/2011 | Ritland |
| 7,988,623 B2 | 8/2011 | Pagliuca et al. |
| 8,007,492 B2 | 8/2011 | DiPoto et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,079,952 B2 | 12/2011 | Fujimoto |
| 8,092,464 B2 | 1/2012 | McKay |
| 8,096,944 B2 | 1/2012 | Harrel |
| 8,202,216 B2 | 6/2012 | Melkent et al. |
| 8,206,357 B2 | 6/2012 | Bettuchi |
| 8,236,006 B2 | 8/2012 | Hamada |
| 8,267,896 B2 | 9/2012 | Hartoumbekis et al. |
| 8,303,492 B2 | 11/2012 | Ito |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,419,625 B2 | 4/2013 | Ito |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,622,894 B2 | 1/2014 | Banik et al. |
| 8,636,655 B1 | 1/2014 | Childs |
| 8,648,932 B2 | 2/2014 | Talbert et al. |
| 8,688,186 B1 | 4/2014 | Mao et al. |
| 8,690,764 B2 | 4/2014 | Clark et al. |
| 8,721,536 B2 | 5/2014 | Marino et al. |
| 8,740,779 B2 | 6/2014 | Yoshida |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,888,689 B2 | 11/2014 | Poll et al. |
| 8,888,813 B2 | 11/2014 | To |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,545 B2 | 1/2015 | To |
| 8,936,605 B2 | 1/2015 | Greenberg |
| 8,952,312 B2 | 2/2015 | Blanquart et al. |
| 8,961,404 B2 | 2/2015 | Ito |
| 8,972,714 B2 | 3/2015 | Talbert et al. |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,036 B2 | 6/2015 | Poll et al. |
| 9,050,037 B2 | 6/2015 | Poll et al. |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,123,602 B2 | 9/2015 | Blanquart |
| 9,131,948 B2 | 9/2015 | Fang et al. |
| 9,144,374 B2 | 9/2015 | Maurice, Jr. |
| 9,153,609 B2 | 10/2015 | Blanquart |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,226,647 B2 | 1/2016 | Sugawara |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,462,234 B2 | 10/2016 | Blanquart et al. |
| 9,486,296 B2 | 11/2016 | Mire et al. |
| 9,492,194 B2 | 11/2016 | Morgenstern Lopez et al. |
| 9,509,917 B2 | 11/2016 | Blanquart et al. |
| 9,510,853 B2 | 12/2016 | Aljuri et al. |
| 9,516,239 B2 | 12/2016 | Blanquart et al. |
| 9,522,017 B2 | 12/2016 | Poll et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,622,650 B2 | 4/2017 | Blanquart |
| 9,629,521 B2 | 4/2017 | Ratnakar |
| 9,641,815 B2 | 5/2017 | Richardson et al. |
| 9,655,605 B2 | 5/2017 | Serowski et al. |
| 9,655,639 B2 | 5/2017 | Mark |

(56) References Cited

U.S. PATENT DOCUMENTS

| | | | |
|---|---|---|---|
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 10,682,130 B2 | 6/2020 | White et al. |
| 2002/0022762 A1 | 2/2002 | Beane et al. |
| 2002/0035313 A1 | 3/2002 | Scirica et al. |
| 2002/0138020 A1 | 9/2002 | Pflueger |
| 2002/0165560 A1 | 11/2002 | Danitz et al. |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |
| 2004/0158286 A1* | 8/2004 | Roux ............... A61B 17/0206 606/205 |
| 2005/0075644 A1 | 4/2005 | DiPoto et al. |
| 2005/0085692 A1 | 4/2005 | Kiehn et al. |
| 2005/0090848 A1 | 4/2005 | Adams |
| 2005/0107671 A1 | 5/2005 | McKinley |
| 2005/0187570 A1 | 8/2005 | Nguyen et al. |
| 2005/0256525 A1 | 11/2005 | Culbert et al. |
| 2006/0041270 A1 | 2/2006 | Lenker et al. |
| 2006/0052671 A1 | 3/2006 | McCarthy |
| 2006/0074445 A1 | 4/2006 | Gerber et al. |
| 2006/0142643 A1 | 6/2006 | Parker |
| 2006/0200186 A1 | 9/2006 | Marchek et al. |
| 2006/0206118 A1 | 9/2006 | Kim et al. |
| 2006/0264895 A1 | 11/2006 | Flanders |
| 2007/0049794 A1 | 3/2007 | Glassenberg et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0162223 A1 | 7/2007 | Clark |
| 2007/0203396 A1 | 8/2007 | McCutcheon et al. |
| 2007/0213716 A1 | 9/2007 | Lenke et al. |
| 2007/0225556 A1 | 9/2007 | Ortiz et al. |
| 2007/0255100 A1 | 11/2007 | Barlow et al. |
| 2007/0260113 A1 | 11/2007 | Otawara |
| 2007/0260184 A1 | 11/2007 | Justis et al. |
| 2008/0015621 A1 | 1/2008 | Emanuel |
| 2008/0033251 A1 | 2/2008 | Araghi |
| 2008/0064921 A1 | 3/2008 | Larkin et al. |
| 2008/0064928 A1 | 3/2008 | Otawara |
| 2008/0081951 A1 | 4/2008 | Frasier et al. |
| 2008/0139879 A1* | 6/2008 | Olson ............... A61B 17/02 600/37 |
| 2008/0147109 A1 | 6/2008 | Kambin et al. |
| 2008/0183189 A1 | 7/2008 | Teichman et al. |
| 2008/0188714 A1 | 8/2008 | McCaffrey |
| 2008/0242930 A1 | 10/2008 | Hanypsiak et al. |
| 2008/0260342 A1 | 10/2008 | Kuroiwa |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0149857 A1 | 6/2009 | Culbert et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2010/0317928 A1 | 12/2010 | Subramaniam |
| 2011/0028791 A1 | 2/2011 | Marino et al. |
| 2011/0054507 A1 | 3/2011 | Batten et al. |
| 2011/0056500 A1 | 3/2011 | Shin et al. |
| 2011/0073594 A1 | 3/2011 | Bonn |
| 2011/0098628 A1 | 4/2011 | Yeung et al. |
| 2011/0106261 A1 | 5/2011 | Chin et al. |
| 2011/0112588 A1 | 5/2011 | Linderman et al. |
| 2011/0125158 A1 | 5/2011 | Diwan et al. |
| 2011/0130634 A1 | 6/2011 | Solitario, Jr. et al. |
| 2011/0201888 A1 | 8/2011 | Verner |
| 2011/0230965 A1 | 9/2011 | Schell et al. |
| 2011/0257478 A1 | 10/2011 | Kleiner et al. |
| 2011/0295070 A1 | 12/2011 | Yasunaga |
| 2011/0319941 A1 | 12/2011 | Bar et al. |
| 2012/0016192 A1 | 1/2012 | Jansen et al. |
| 2012/0029412 A1 | 2/2012 | Yeung et al. |
| 2012/0095296 A1 | 4/2012 | Trieu et al. |
| 2012/0101338 A1 | 4/2012 | O'Prey et al. |
| 2012/0111682 A1 | 5/2012 | Andre |
| 2012/0116170 A1 | 5/2012 | Vayser et al. |
| 2012/0157788 A1* | 6/2012 | Serowski ............... A61B 17/02 600/229 |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0265022 A1 | 10/2012 | Menn |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172674 A1 | 7/2013 | Kennedy, II et al. |
| 2013/0172676 A1 | 7/2013 | Levy et al. |
| 2013/0211202 A1 | 8/2013 | Perez-Cruet et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0304106 A1 | 11/2013 | Breznock |
| 2014/0025121 A1 | 1/2014 | Foley et al. |
| 2014/0066940 A1 | 3/2014 | Fang et al. |
| 2014/0074170 A1 | 3/2014 | Mertens et al. |
| 2014/0088367 A1 | 3/2014 | DiMauro et al. |
| 2014/0142584 A1 | 5/2014 | Sweeney |
| 2014/0148647 A1 | 5/2014 | Okazaki |
| 2014/0163319 A1 | 6/2014 | Blanquart et al. |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0221749 A1 | 8/2014 | Grant et al. |
| 2014/0257296 A1 | 9/2014 | Lopez |
| 2014/0257332 A1 | 9/2014 | Zastrozna |
| 2014/0257489 A1 | 9/2014 | Warren et al. |
| 2014/0275793 A1 | 9/2014 | Song |
| 2014/0275799 A1 | 9/2014 | Schuele |
| 2014/0276840 A1 | 9/2014 | Richter et al. |
| 2014/0276916 A1 | 9/2014 | Ahluwalia et al. |
| 2014/0277204 A1 | 9/2014 | Sandhu |
| 2014/0285644 A1 | 9/2014 | Richardson et al. |
| 2014/0318582 A1 | 10/2014 | Mowlai-Ashtiani |
| 2014/0336764 A1 | 11/2014 | Masson et al. |
| 2014/0357945 A1 | 12/2014 | Duckworth |
| 2014/0378985 A1 | 12/2014 | Mafi |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0133727 A1 | 5/2015 | Bacich et al. |
| 2015/0164496 A1 | 6/2015 | Karpowicz et al. |
| 2015/0216593 A1 | 8/2015 | Biyani |
| 2015/0223671 A1 | 8/2015 | Sung et al. |
| 2015/0223676 A1 | 8/2015 | Bayer et al. |
| 2015/0230697 A1 | 8/2015 | Phee et al. |
| 2015/0238073 A1 | 8/2015 | Charles et al. |
| 2015/0272694 A1 | 10/2015 | Charles |
| 2015/0313585 A1 | 11/2015 | Abidin et al. |
| 2015/0335389 A1* | 11/2015 | Greenberg ............. A61B 90/50 606/1 |

(56) References Cited

U.S. PATENT DOCUMENTS

| | | |
|---|---|---|
| 2015/0342621 A1 | 12/2015 | Jackson, III |
| 2015/0366552 A1 | 12/2015 | Sasaki et al. |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0256036 A1 | 9/2016 | Gomez et al. |
| 2016/0287264 A1 | 10/2016 | Chegini et al. |
| 2016/0296220 A1 | 10/2016 | Mast et al. |
| 2016/0345952 A1 | 12/2016 | Kucharzyk et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0007294 A1 | 1/2017 | Iwasaka et al. |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0105770 A1 | 4/2017 | Woolley et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2017/0245930 A1 | 8/2017 | Brannan et al. |
| 2017/0280969 A1 | 10/2017 | Levy et al. |
| 2017/0296038 A1 | 10/2017 | Gordon et al. |
| 2018/0008138 A1 | 1/2018 | Thommen et al. |
| 2018/0008253 A1 | 1/2018 | Thommen et al. |
| 2018/0014858 A1 | 1/2018 | Biester et al. |
| 2018/0098788 A1 | 4/2018 | White et al. |
| 2018/0098789 A1 | 4/2018 | White et al. |
| 2018/0110503 A1 | 4/2018 | Flock et al. |
| 2018/0153592 A1 | 6/2018 | Larson |
| 2018/0214016 A1 | 8/2018 | Thommen et al. |
| 2018/0333061 A1 | 11/2018 | Pracyk et al. |
| 2019/0209154 A1 | 7/2019 | Richter et al. |
| 2019/0216454 A1 | 7/2019 | Thommen et al. |

FOREIGN PATENT DOCUMENTS

| | | |
|---|---|---|
| DE | 299 16 026 U1 | 11/1999 |
| EP | 0 537 116 A1 | 4/1993 |
| EP | 0 807 415 A2 | 11/1997 |
| GB | 2481727 A | 1/2012 |
| JP | 05-207962 A | 8/1993 |
| JP | 08-278456 A | 10/1996 |
| JP | 2007-007438 A | 1/2007 |
| JP | 2008-508943 A | 3/2008 |
| JP | 2011-512943 A | 4/2011 |
| JP | 2013-538624 A | 10/2013 |
| JP | 2014-517710 A | 7/2014 |
| JP | 2015-500680 A | 1/2015 |
| WO | 96/29014 A1 | 9/1996 |
| WO | 97/34536 A2 | 9/1997 |
| WO | 01/56490 A1 | 8/2001 |
| WO | 01/89371 A1 | 11/2001 |
| WO | 02/02016 A1 | 1/2002 |
| WO | 2004/103430 A2 | 12/2004 |
| WO | 2006/017507 A2 | 2/2006 |
| WO | 2007/059068 A1 | 5/2007 |
| WO | 2008/121162 A1 | 10/2008 |
| WO | 2009/033207 A1 | 3/2009 |
| WO | 2009/108318 A2 | 9/2009 |
| WO | 2010138083 A1 | 12/2010 |
| WO | 2012/040239 A1 | 3/2012 |
| WO | 2012/122294 A1 | 9/2012 |
| WO | 2013/033426 A2 | 3/2013 |
| WO | 2013/059640 A1 | 4/2013 |
| WO | 2013/074396 A1 | 5/2013 |
| WO | 2014/050236 A1 | 4/2014 |
| WO | 2014/100761 A2 | 6/2014 |
| WO | 2014/185334 A1 | 11/2014 |
| WO | 2015/175635 A1 | 11/2015 |
| WO | 2016/111373 A1 | 7/2016 |
| WO | 2016/131077 A1 | 8/2016 |
| WO | 2016/168673 A1 | 10/2016 |
| WO | 2016/201292 A1 | 12/2016 |
| WO | 2017/006684 A1 | 1/2017 |
| WO | 2017/015480 A1 | 1/2017 |
| WO | 2017/083648 A1 | 5/2017 |
| WO | 2018/165365 A2 | 9/2018 |

OTHER PUBLICATIONS

Hott, J. S., et al., "A new table-fixed retractor for anterior odontoid screw fixation: technical note," J Neurosurg (Spine 3), 2003, v. 98, pp. 118-120.

International Search Report and Written Opinion for Application No. PCT/US2015/043554, dated Nov. 19, 2015 (8 pages).

International Search Report and Written Opinion for Application No. PCT/US2015/048485, dated Feb. 9, 2016. (16 pages).

International Search Report and Written Opinion for Application No. PCT/US2015/060978, dated Feb. 15, 2016 (8 pages).

Invitation to Pay Additional Fees for Application No. PCT/US2016/050022, mailed Nov. 3, 2016 (2 pages).

International Search Report and Written Opinion for Application No. PCT/US2016/050022, dated Feb. 1, 2017 (19 pages).

International Preliminary Report on Patentability issued for Application No. PCT/US216/050022, mailed Mar. 15, 2018.

Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.

Jung, K., et al., "A hands-free region-of-interest selection interface for solo surgery with a wide-angle endoscope: preclinical proof of concept," Surg Endosc, 2017, v. 31, pp. 974-980.

Regan, J. M. et al., "Burr Hole Washout versus Craniotomy for Chronic Subdural Hematoma: Patient Outcome and Cost Analysis," Plos One, Jan. 22, 2015, DOI:10.1371/journal.pone.0115085.

Shalayev, S. G. et al, "Retrospective analysis and modifications of retractor systems for anterior odontoid screw fixation," Neurosurg Focus 16 (1)Article 14, 2004, pp. 1-4.

Extended European Search Report for Application No. 16843037.9; dated Mar. 14, 2019 (8 pages).

International Search Report and Written Opinion for Application No. PCT/US18/21466 dated Jul. 3, 2018 (8 pages).

International Search Report and Written Opinion for Application No. PCT/US18/21454, dated Jul. 3, 2018 (16 pages).

International Search Report and Written Opinion for Application No. PCT/US18/21449, dated Aug. 27, 2018 (13 pages).

International Search Report and Written Opinion for Application No. PCT/US18/47136, dated Jan. 23, 2019 (9 pages).

International Search Report and Written Opinion for Application No. PCT/EP2020/056706, dated Jun. 9, 2020 (17 pages).

International Search Report and Written Opinion for Application No. PCT/US19/18700, dated May 3, 2019 (7 pages).

International Search Report and Written Opinion for Application No. PCT/US2018/018905, dated May 7, 2018 (10 pages).

International Search Report and Written Opinion issued for Application No. PCT/US2018/021472, dated Jul. 19, 2018.

Japanese Office Action issued in Appln. No. JP 2018-511695, dated May 26, 2020 (21 pages).

\* cited by examiner

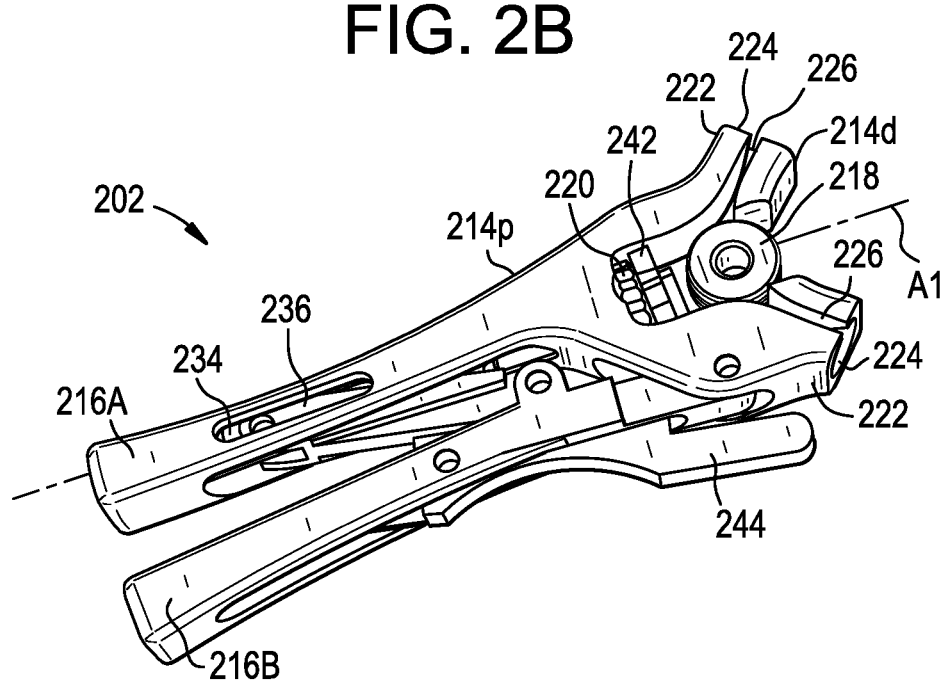
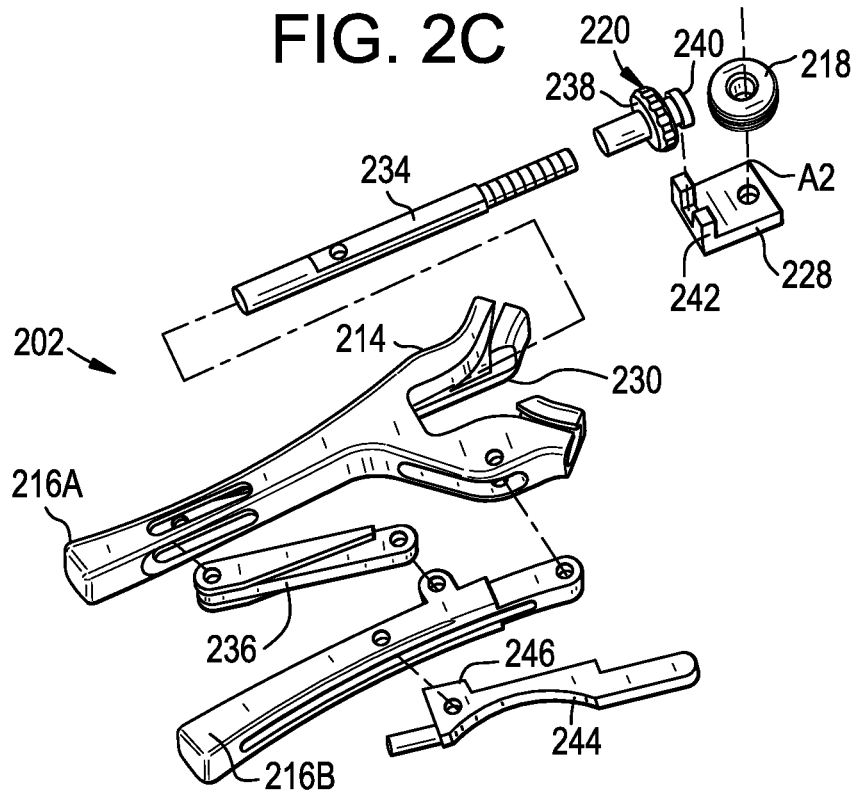

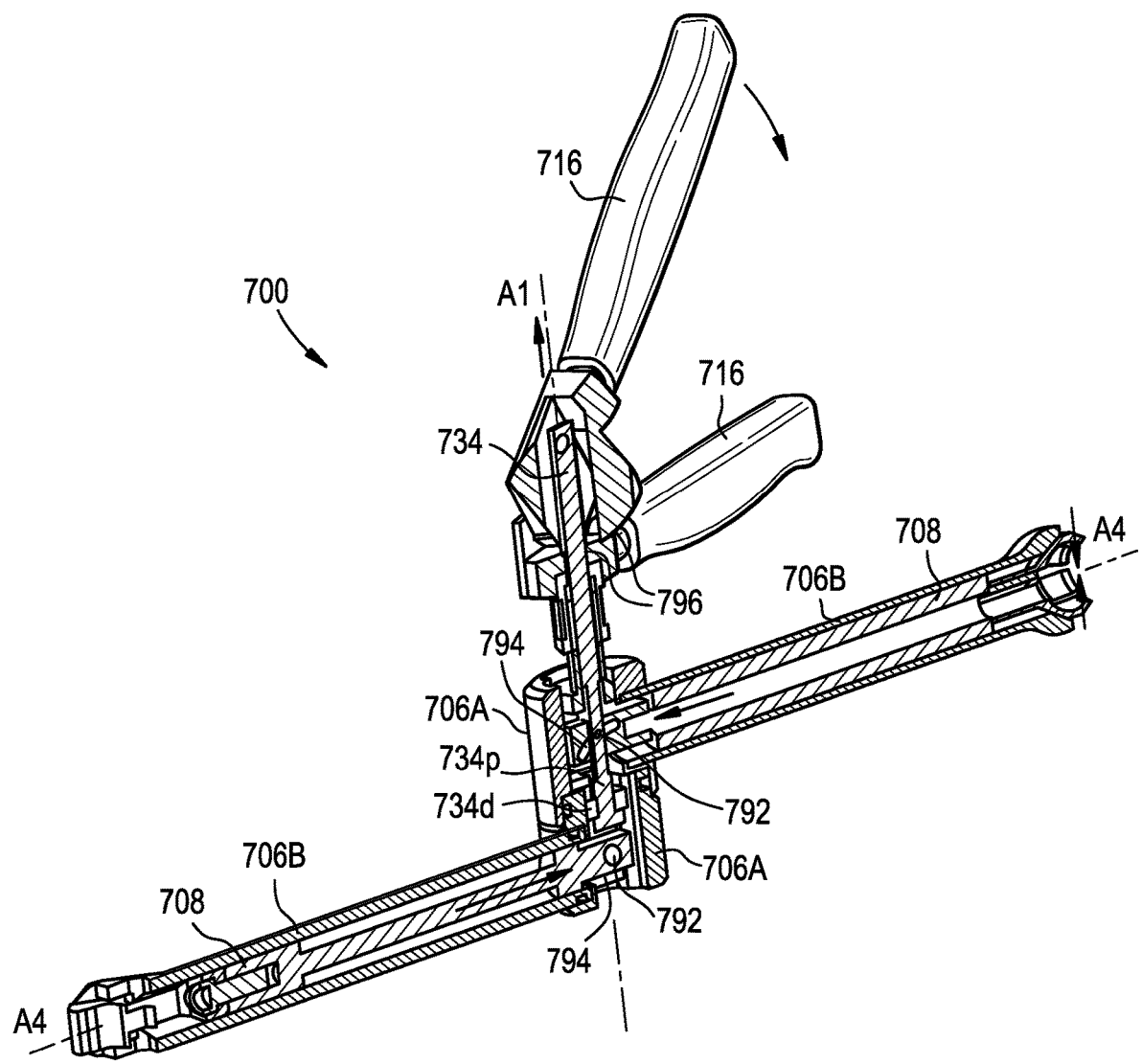

SURGICAL INSTRUMENT CONNECTORS AND RELATED METHODS

CROSS-REFERENCE TO RELATED APPLICATIONS

The present application claims priority to U.S. Provisional Application No. 62/468,475 filed on Mar. 8, 2017, which is hereby incorporated by reference herein. The present application is also a continuation-in-part of U.S. application Ser. No. 15/437,792 filed on Feb. 21, 2017, which is a continuation-in-part of U.S. application Ser. No. 15/254,877 filed on Sep. 1, 2016, which claims priority to U.S. Provisional Application No. 62/214,297 filed on Sep. 4, 2015, each of which is hereby incorporated by reference herein.

FIELD

Surgical instrument connectors and related methods are disclosed herein, e.g., for connecting a surgical access device to a support or anchor.

BACKGROUND

There are many instances in which it may be desirable to connect or link one instrument or object to another instrument or object. In surgical applications, for example, it may be desirable to stabilize an access device (e.g., a cannula, a retractor, etc.) positioned in an incision formed in a patient by connecting the access device to a support.

SUMMARY

Connectors for connecting or linking one instrument or object to one or more other instruments or objects are disclosed herein. In some embodiments, a connector can include a first arm with a first attachment feature for attaching to a first object, such as a surgical access device, and a second arm with a second attachment feature for attaching to a second object, such as a support. The connector can have an unlocked state, in which the position and orientation of the access device can be adjusted relative to the support, and a locked state in which movement of the access device relative to the support is prevented or limited. Locking the connector can also be effective to clamp or otherwise attach the connector to the access device and the support, or said attachment can be independent of the locking of the connector.

In some embodiments, a connector can include at least one arm having a plurality of nested segments and an attachment feature for attaching an instrument to the arm; and a handle, wherein the handle is movable between a first position in which the plurality of nested segments are movable relative to one another and a second position in which the plurality of nested segments are fixed relative to one another.

The at least one arm can include first and second arms having respective first and second attachment features, wherein the attachment features are movable in one or more degrees of freedom relative to one another when the handle is in the first position, and wherein said one or more degrees of freedom are locked when the handle is in the second position. Movement of the handle to the second position can be effective to lock movement of the first arm, lock movement of the second arm, lock the first attachment feature to a first instrument, and lock the second attachment feature to a second instrument. Movement of the handle to the first position can be effective to restore movement of the first arm, restore movement of the second arm, unlock the first attachment feature from the first instrument, and unlock the second attachment feature from the second instrument.

The connector can include an actuation wire extending through the plurality of nested segments, wherein the handle in the second position increases tension on the actuation wire to fix the segments and wherein the handle in the first position decreases tension on the actuation wire to allow movement between the segments. The actuation wire can be coupled to the attachment feature such that increasing tension on the actuation wire closes the attachment feature. The handle can include a wire track in which a portion of the actuation wire is disposed, the wire track being open to an exterior side surface of the handle to allow the wire to be introduced laterally into the wire track. The handle can include a bearing element engaged with the actuation wire. Movement of the handle can cause translation of the bearing element along a tension axis, thereby increasing or decreasing tension applied to the actuation wire. The handle can include first and second branches, each being operatively associated with an arm of the connector, the branches defining a cavity therebetween. The bearing element can be mounted on a plate slidably disposed in the cavity. Opposed edges of the plate can be slidably disposed within corresponding tracks formed in the branches.

The connector can include an actuation shaft disposed within a lumen of the handle. The connector can include a linkage bar coupled to a movable handle lever of the handle and to the actuation shaft. The connector can include an adjustment knob threadably mated to the actuation shaft to form an assembly, wherein rotation of the adjustment knob adjusts the length of the assembly as measured along a tension axis, thereby adjusting the amount of tension applied to an actuation wire of the at least one arm when the handle is moved between the first and second positions. The connector can include a locking mechanism for selectively maintaining the handle in at least one of the first and second positions. The locking mechanism can include a movable handle lever pivotally coupled to a linkage bar and configured to enter an over-center condition when the handle is in the second position. The plurality of nested segments can be configured to pitch, yaw, and roll relative to one another when the handle is in the first position. The attachment feature can define a central opening through which an instrument or other object can be received. The attachment feature can apply a pre-load or provisional friction fit to an object received therein when the handle is in the first position.

The attachment feature can include at least one of a ring clamp, a lasso, an end-loading jaw, a side-loading jaw, and a spherical clamp. The handle can be biased towards the second position. The connector can include a spring element that biases the handle towards the second position, wherein the spring element urges an actuation wire extending through the at least one arm in a proximal direction to apply tension thereto. Moving the handle to the first position can compress the spring element to reduce tension applied to the actuation wire. The handle can include a scissor linkage that expands to compress the spring element when the handle is in the first position. The at least one arm can include first and second arms, and the handle can include a fixed handle lever, a first movable handle lever movable with respect to the fixed handle lever to lock the first arm, and a second movable handle lever movable with respect to the fixed handle lever to lock the second arm.

In some embodiments, a surgical method can include positioning a surgical access device relative to a patient; attaching the access device to a first arm of a connector; attaching a second arm of the connector to a support; articulating a plurality of nested segments of at least one of the first and second arms to adjust a position and orientation of the access device relative to the support; and locking the connector to maintain the access device and the support in the adjusted position and orientation.

The support can include an anatomical structure of the patient or an implant implanted in the patient. The support can be mounted to a pedicle of the patient. The connector can provide a range of movement between the access device and the support that is unrestricted within the environment of lumbar posterior access spine surgery. Locking the connector can lock multiple degrees of freedom between the access device and the support simultaneously with a single action. Locking the connector can be effective to, simultaneously and with a single action, lock the access device to the first arm, lock the support to the second arm, and lock multiple degrees of freedom between the access device and the support. Positioning the access device can include inserting the access device into a patient such that a distal end of the access device is disposed within or proximate to an intervertebral disc space of the patient. The support can be mounted to a vertebral bone structure disposed on a side of the disc space that is ipsilateral to the access device. The support can be mounted to a vertebral bone structure disposed on a side of the disc space that is contralateral to the access device. At least a portion of the second arm can be positioned beneath a skin surface of the patient. The method can include delivering a fusion cage through the access device to an intervertebral disc space of the patient. The method can include performing a discectomy through the access device.

Locking the connector can be done by applying a user input force to the connector using only one hand. Locking the connector can include removing a user input force from first and second handle levers of the connector. In some embodiments, locking the connector does not move the access device or the support relative to the patient. The access device can include a tissue retractor. Positioning the access device can include supporting or retracting tissue using the access device. The tissue can be an abdominal shelf of the patient, a breast of the patient, a rectum of the patient, or an anus of the patient. The access device can include a trans-anal port. The method can include using a third arm of the connector to hold a light source or an instrument inserted into the access device. The method can include positioning a distal end of the access device in proximity to an odontoid of the patient, the connector maintaining the access device at a fixed trajectory relative to the odontoid, and inserting a screw through the access device and into the odontoid.

The access device can include a first skull port and the support can include a second skull port. The method can include delivering material through the first skull port and aspirating material from the second skull port. The method can include evacuating at least one of an epidural hematoma, a subdural hematoma, a hygroma, frontal bone, and parietal bone through at least one of the skull ports. The support can include a screw or nail previously implanted in the patient. The support can include a bone plate. The method can include delivering a bone anchor through the access device and into an opening formed in the bone plate. The support can include an implanted fixation construct. The method can include delivering a component of the construct through the access device and attaching said component to the implanted fixation construct.

The method can include positioning a distal end of the access device in proximity to a bone fracture of the patient, the connector maintaining the access device at a fixed trajectory relative to the fracture, and inserting a screw or nail through the access device to reduce the fracture. The fracture can be in a tibial plateau, a navicular bone, or a long bone. The method can include holding a bone fragment in place using the access device while delivering the screw or nail through the access device. The method can include holding a bone fragment in place using a third arm of the connector while delivering a screw or nail through the access device. The method can include attaching a bone fragment to the connector, manipulating an arm of the connector to position the bone fragment in a desired location relative to the fracture, and locking the connector to hold the bone fragment in the desired location. The method can include positioning a distal end of the access device in alignment with an opening formed in an intramedullary device implanted in the patient, the connector maintaining the access device at a fixed trajectory relative to the opening, and delivering a locking screw through the access device into the opening. The support can include the intramedullary device or an inserter instrument coupled thereto.

In some embodiments, a surgical method can include inserting a first needle into a patient; inserting a second needle into the patient; coupling the first and second needles to respective arms of a connector, the arms comprising a plurality of nested segments and the connector being selectively lockable to prevent movement between the plurality of nested segments; and locking the connector to automatically position the first and second needles in a predetermined position and orientation relative to one another and to lock movement between the first and second needles. The predetermined orientation can be one in which the first and second needles are parallel.

In some embodiments, a surgical method can include forming first and second discrete skin portals into a joint of a patient; inserting a visualization device through the first skin portal; inserting a surgical instrument through the second skin portal; attaching the visualization device to a first arm of a connector; attaching the surgical instrument to a second arm of the connector; positioning a distal end of the instrument within a field of view of the visualization device; and locking the connector to prevent relative movement of the first and second arms and thereby maintain the distal end of the instrument in the field of view of the visualization device.

The joint can include a knee joint. The visualization device can include an arthroscope. The surgical instrument can include a shaver, cutter, or drill.

In some embodiments, a surgical method can include implanting a bone anchor in a pedicle of a patient's spine, the bone anchor having an extension extending proximally therefrom; attaching a first arm of a connector to the extension; inserting an access device via a transforaminal approach to position a distal end of the access device in alignment with an intervertebral disc space of the patient's spine; attaching a second arm of the connector to the access device; articulating the first and second arms of the connector at a plurality of nested segments thereof to adjust a position of the access device relative to the extension; locking the connector to restrict articulation of the plurality of nested segments and maintain a relative positioning of the access device and the extension; and passing a fusion cage through the access device and into the disc space.

The method can include applying a user input force to the connector to unlock the connector; adjusting the relative positioning of the access device and the extension; and removing the user input force from the connector, thereby automatically relocking the connector.

BRIEF DESCRIPTION OF THE DRAWINGS

FIG. 2B is a perspective view of a handle assembly of the connector of FIG. 2A;

FIG. 2C is an exploded perspective view of the handle assembly of FIG. 2B;

FIG. 7C is a sectional perspective view of the connector of FIG. 7A;

DETAILED DESCRIPTION

Figure 1:
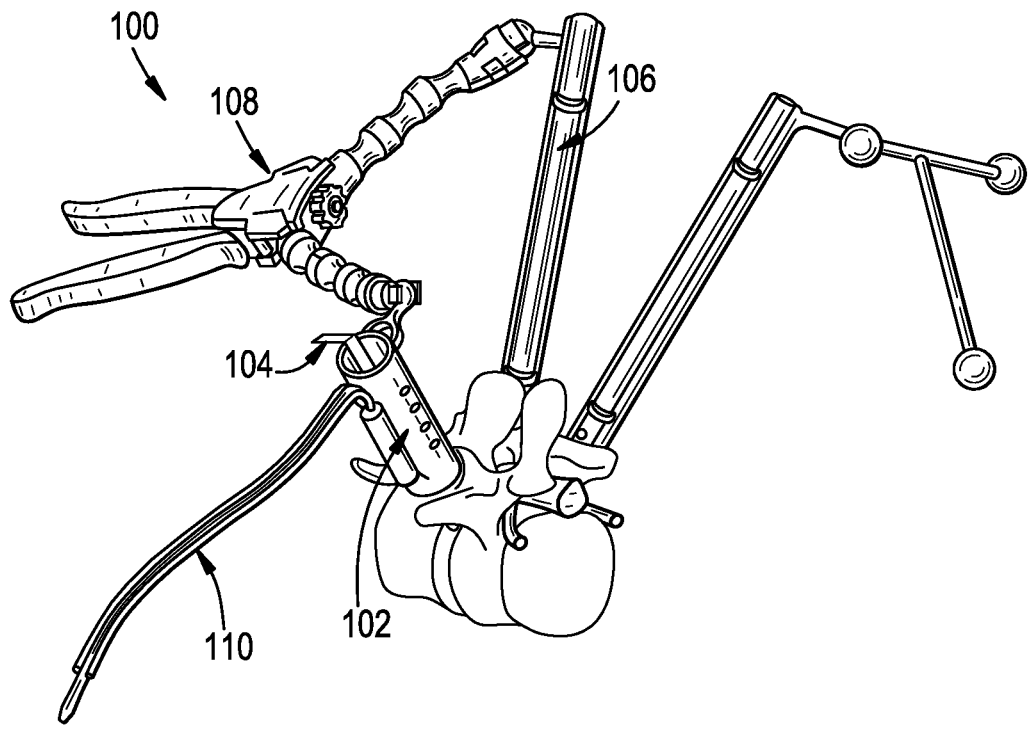
FIG. 1 is a perspective view of a surgical system in use to perform a surgical procedure on a patient's spine.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Connectors for connecting or linking one instrument or object to one or more other instruments or objects are disclosed herein. In some embodiments, a connector can include a first arm with a first attachment feature for attaching to a first object, such as a surgical access device, and a second arm with a second attachment feature for attaching to a second object, such as a support. The connector can have an unlocked state, in which the position and orientation of the access device can be adjusted relative to the support, and a locked state in which movement of the access device relative to the support is prevented or limited. Locking the connector can also be effective to clamp or otherwise attach the connector to the access device and the support, or said attachment can be independent of the locking of the connector.

The connectors described herein can include any one or more of the following features. The connector can be configured to rigidly fix the position and orientation between two or more attached objects, e.g., such that the position and orientation between the attached objects does not change when those objects are subjected to the manipulations and forces that are typical of spinal surgery. The connector can be configured to lock and unlock with a simple one-handed manipulation. The connector can be configured such that locking and unlocking the connector does not apply significant resultant forces on the attached objects, other than forces associated with attachment of those objects to the connector. In other words, the connector can be configured such that it can be locked and/or unlocked without appreciably moving the objects attached thereto relative to the patient. The connector can be attached to an access device and a pedicle-mounted support and can provide a range of movement therebetween that is unrestricted within the environment of lumbar posterior access spine surgery. The connector can be configured to attach to various objects with a simple click-on or dock-on attachment mechanism.

The connector can allow for a strong connection to attached objects, minimizing any toggle or movement between the object and the connector when the connector is locked. The connector can provide mechanical advantage in locking and/or unlocking the connector, e.g., to obtain a locking force that is significantly greater than the user input force. The connector can allow for a high range of adjustability or freedom of movement between attached objects when the connector is unlocked. The connector can be configured to quickly and efficiently lock multiple degrees of freedom (DOF) between attached objects. The connector can be configured to quickly and efficiently attach and detach from objects. The connector can be configured to simultaneously lock onto multiple objects and to lock the position and orientation between those objects with the same single action. The connector can be configured such that the connector can be made completely flexible or completely stiff quickly and easily using a simple one-handed actuation motion. This can allow the positioning of attached objects to be adjusted with minimal disruption to surgical flow.

In some embodiments, a connector can be actuated to simultaneously, and in a single action, lock or unlock (i) a first instrument to the connector, (ii) a second instrument to the connector, and (iii) one or more degrees of freedom between the first and second instruments.

The connectors described herein can be used in various types of surgery, including spinal surgery. Exemplary spinal surgeries can include lumbar spine minimally-invasive surgery (MIS). The connectors described herein can be used to connect an access channel, retractor, tube, etc. to the anatomy of the vertebral segment (e.g., via a pedicle post or other support) that is being operated on, instead of or in addition to connecting it to the operating table. In some arrangements, the connector can be used to connect the access device to the operating table.

The connectors described herein can be configured to allow the access device to remain fixed relative to the patient's anatomy, even if the position of the patient's anatomy changes during the surgery. The connector can thus maintain a consistent field of view through the access device, eliminating the need to readjust the access device if the patient moves. The connector can have a slim or low-profile form factor as compared to traditional retractor equipment.

The connectors described herein can support an access device relative to a patient to facilitate hands-free operation. In other words, a surgeon or other user is not required to manually hold the connector or the access device during use, and therefore the user's hands can be freed to perform other tasks. The connector can be used to support an access device having an integrated or attached camera or other visualization device, such that the visualization device is supported by the access device in a hands-free manner. Thus, the connector can facilitate hands-free surgical visualization, as the surgeon or other user is not required to manually hold the connector, the access device, or the visualization device during use in a surgery.

The connectors described herein can be configured to attach a first part (such as an anatomic anchor) to a second part (such as an access tube or retractor) in a way that is easy and quick for the user to attach the connector, detach the connector, and to change the position between the two parts during the surgery.

FIG. 1 illustrates an exemplary surgical system 100 in which the devices and methods described herein can be used, though it will be appreciated that such devices and methods can be used in various other applications instead or in addition. Further details on the system of FIG. 1 can be found in U.S. application Ser. No. 15/437,792 filed on Feb. 21, 2017, which is hereby incorporated by reference herein. The system 100 can be used in various surgical procedures, including spinal surgeries such as microsurgical bone resection, spinal decompression, spinal fusion, and the like. In general, the system 100 can include any one or more of an access device 102, a tissue retractor 104, a pedicle post or other anchor 106, a connector 108, and a camera 110. Exemplary access devices 102 are disclosed in U.S. application Ser. No. 15/786,858 entitled DEVICES AND METHODS FOR PROVIDING SURGICAL ACCESS and filed on an even date herewith. Exemplary tissue retractors 104 are disclosed in U.S. application Ser. No. 15/786,846 entitled DEVICES AND METHODS FOR SURGICAL RETRACTION and filed on an even date herewith. Exemplary anchors 106 are disclosed in U.S. application Ser. No. 15/786,891 entitled SURGICAL ACCESS PORT STABILIZATION and filed on an even date herewith. Exemplary connectors 108 are disclosed herein. Exemplary cameras 110 are disclosed in U.S. application Ser. No. 15/692,845 entitled SURGICAL VISUALIZATION SYSTEMS AND RELATED METHODS and filed on Aug. 31, 2017. Each of the above applications is hereby incorporated by reference herein.

An exemplary method of using the system 100 of FIG. 1 can include any one or more of the following steps, performed in any of a variety of sequences: a) making an incision in a skin of a patient; b) percutaneously inserting through the incision an access device 102 having a substantially tubular shape (such as a tube or a multi-slotted retractor), the access device having a length adapted to extend from the incision to a border between sensitive and insensitive tissue (e.g., a superior articular process (SAP), or a lamina) in the spine of the patient; c) stabilizing the access device to an anchor 106 (e.g., a pedicle anchor) using a connector 108; d) inserting an access device integrated optical visualization instrument 110; e) resecting a portion of the superior articular process, and/or performing a microsurgical decompression procedure; f) inserting or deploying a tissue retractor 104 through or from the access device so that a distal end portion of the tissue retractor extends to the intervertebral disc, the retractor having an outer surface; g) contacting the outer surface of the retractor to a nerve root to shield the nerve root; h) microsurgically decompressing any tissue deemed to be causing nerve impingement; i) extracting intervertebral disc material including removing cartilaginous material from the vertebral endplates; j) inserting an interbody device; and k) deploying a mechanism of stabilization to stabilize the intervertebral segment.

FIGS. 2A-2G illustrate an exemplary connector 200 that can be used to connect a first object to a second object. For example, the connector 200 can be used to connect first and second surgical instruments. By way of further example, the connector 200 can be used in the system 100 described above, e.g., to connect the access device 102 to the support or anchor 106.

As shown, the connector 200 can include a handle assembly 202 and an arm assembly 204. The arm assembly 204 can include at least one arm 206 configured to transition between a fixed state and a movable state. The arm 206 can include an attachment feature 208 for attaching the arm to an instrument, a support, or some other object. The arm 206 can include a first end coupled to the handle assembly 202 and a second end at which the attachment feature 208 is disposed. The arm 206 can include a plurality of nested segments 210 threaded onto a wire or cable 212. The wire or cable 212 can also be operatively coupled with the attachment feature 208 of the arm 206. In an exemplary arrangement, each nested segment 210 of the arm 206 can pivot or rotate with respect to adjacent segments, allowing movement of the second end of the arm relative to the first end of the arm. In arrangements with multiple arms 206, each arm can be independently movable, such that an object coupled to a first arm can be moved relative to an object coupled to a second arm in at least six degrees of freedom. In use, tension on the wire 212 can be relaxed to allow the arm 206 to articulate. Relaxing the tension on the wire 212 can also be effective to release the attachment feature 208 from an object received therein. When a desired positioning of the arm 206 is achieved, tension can be increased or restored to the wire 212 to lock the arm in the desired position. Increasing tension on the wire 212 can also be effective to close, clamp, or otherwise engage the attachment feature 208 with an object received therein.

The handle assembly 202 can be actuated by a user to selectively apply or release tension, or to selectively increase or decrease tension, from the wire 212 of the arm assembly 204. The handle assembly 202 can include a handle frame 214 and one or more handle levers 216. While a fixed handle lever 216A and a movable handle lever 216B are shown, it will be appreciated that the handle assembly 202 can include any number of fixed and/or movable handle levers. The handle assembly 202 can include a pulley or other bearing element 218 that is engaged with the wire 212 of the arm assembly 204. Actuation or movement of the handle assembly 202 can cause the pulley 218 to translate along a tension axis A1 to increase or decrease tension on the wire 212. For example, squeezing the handle levers 216 together to a "closed" position can cause the pulley 218 to translate along the axis A1 in a proximal direction, applying tension to the wire 212 of the arm assembly 204. Moving the handle levers 216 apart to an "open" position can cause the pulley 218 to translate along the axis A1 in a distal direction, relaxing the tension applied to the wire 212. An adjustment knob 220 can be rotated to fine-tune the amount of tension applied to the wire 212 in the closed and open positions of the handle assembly 202. As described further below, in other arrangements, squeezing the handle levers 216 together can be effective to reduce the tension on the wire 212 and releasing the handle levers can be effective to increase the tension on the wire.

In some arrangements, the handle assembly 202 can be reusable and the arm assembly 204 can be a single-use disposable. The connector 200 can be provided as a kit with a plurality of different handle assemblies and/or a plurality of different arm assemblies, with the components of the kit being freely interchangeable by the user as needed or desired.

Figure 2A:
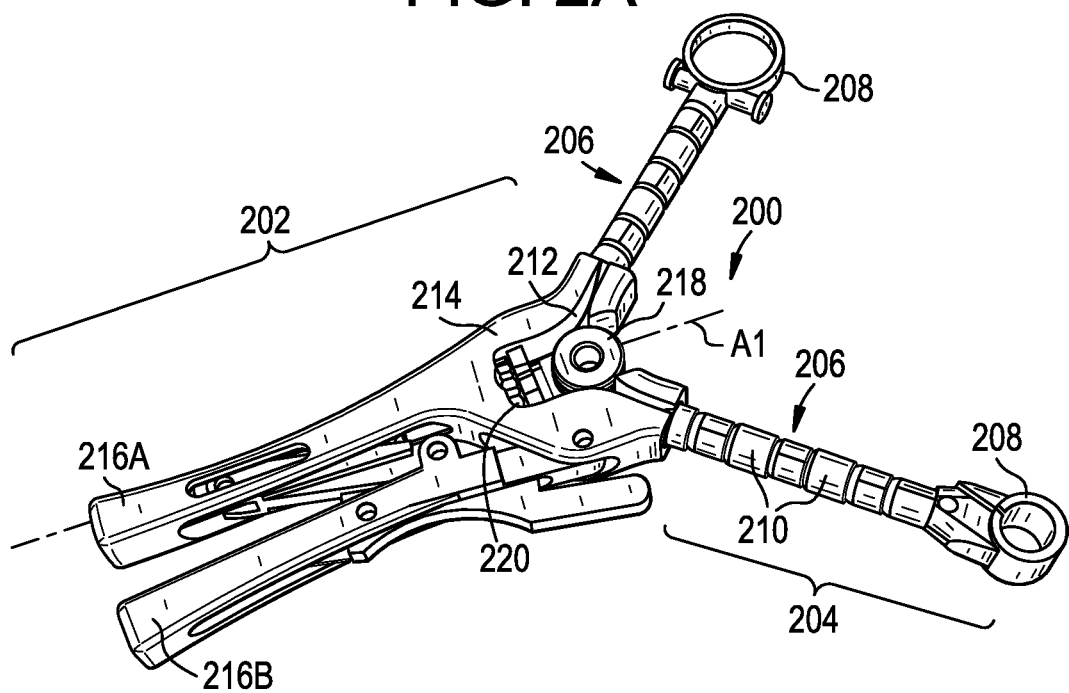
FIG. 2A is a perspective view of a connector.
Figure 2D:
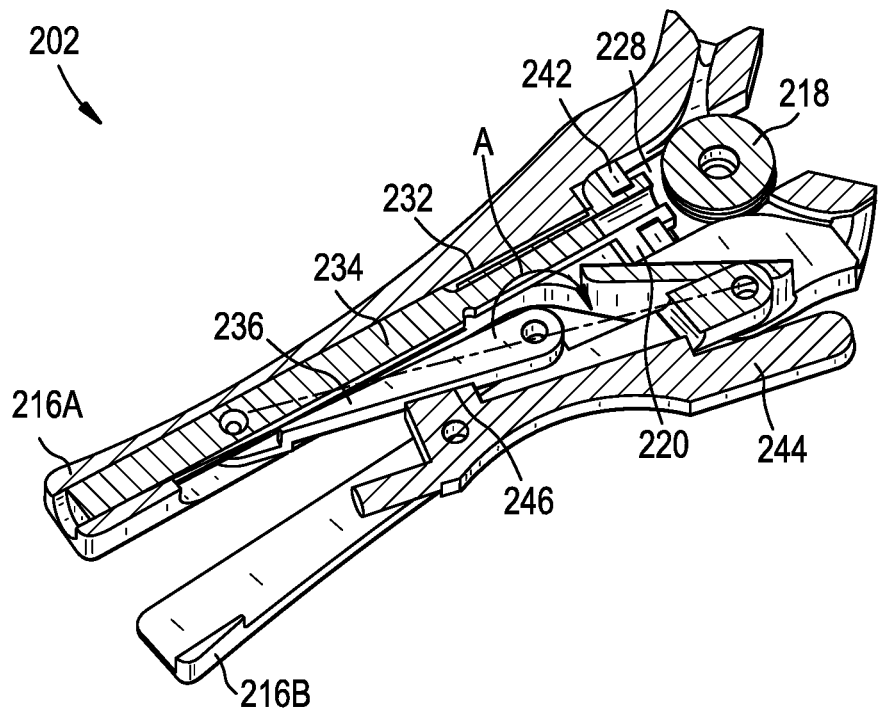
FIG. 2D is a sectional perspective view of the handle assembly of FIG. 2B.

The handle assembly 202 is shown in greater detail in FIGS. 2B-2D. The handle frame 214 can include proximal and distal ends 214p, 214d that define a longitudinal or proximal-distal axis A1. The distal end 214d of the handle frame 214 can define one or more branches 222, each being operatively associated with a respective arm 206 of the arm assembly 204. In the illustrated embodiment, the handle frame 214 includes first and second branches 222 associated with first and second arms 206 of the arm assembly 204, respectively. Each branch 222 can include a mating interface 224 that receives the proximal-most segment 210 of its respective arm 206. The mating interface 224 can be a spherical or substantially spherical depression or protrusion. The mating interface 224 can include a key or a keyway configured to receive a counterpart component of the proximal-most segment 210 of the arm 206, e.g., to limit movement of said segment relative to the branch 222 in one or more degrees of freedom. The branch 222 can include a wire track 226 through which the wire 212 of the arm assembly 204 can be routed. The wire track 226 can be open to at least one exterior surface of the handle frame 214. This can allow the wire 212 to be easily side-loaded or otherwise introduced into the wire track 226 during assembly of the handle frame 214 to the arm assembly 204.

The tension pulley 218 can be mounted within a cavity defined between the branches 222 of the handle frame 214. The tension pulley 218 can be a cylindrical or substantially cylindrical body with a circumferential track formed in an exterior surface thereof for receiving the wire 212. The tension pulley 218 can be mounted to a sliding plate 228 via a pin or axle received through a central opening of the tension pulley. The tension pulley 218 can be rotatable relative to the plate 228 about an axis A2, or can be fixed relative to the plate. Opposed lateral edges of the plate 228 can include a mating feature slidably mounted within a counterpart mating feature of the branches 222. For example, the opposed lateral edges of the plate 228 can act as male mating features and can be received with respective grooves 230 formed in the branches 222 to act as female mating features. The edges of the plate 228 can be chamfered or tapered as shown, and the slots 230 can have a corresponding but negative geometry. In other arrangements, the branches 222 can include a raised ridge received within a corresponding slot formed in the plate 228. The plate 228 can be slidably mounted to the branches 222, such that the plate can translate relative to the handle frame 214 along the axis A1.

Movement of the plate 228 and, by extension, the tension pulley 218 along the axis A1 can be controlled by actuation of one or more handle levers 216 of the handle assembly 202. While a fixed handle lever 216A and a movable handle lever 216B are shown, it will be appreciated that the handle assembly 202 can include any number of fixed and/or movable handle levers. The movable handle lever 216B can be pivotally mounted to the handle frame 214. For example, the distal end of the movable handle lever 216B can be attached to the proximal end of the handle frame 214 by a pivot pin. The fixed handle 216A can be formed integrally with the handle frame 214, or can be rigidly fixed thereto.

The handle frame 214 can define an interior channel or lumen 232 in which an actuation shaft 234 is slidably disposed such that the actuation shaft can translate along the axis A1 relative to the handle frame. The channel 232 can extend into the fixed handle lever 216A. A linkage bar 236 can be coupled to the movable handle lever 216B and to the actuation shaft 234 via respective pivot pins.

The distal end of the actuation shaft 234 can be received within an opening formed in the adjustment knob 220. The actuation shaft 234 can include an external thread that engages with an internal thread of the adjustment knob 220. The actuation shaft 234 and the adjustment knob 220 can collectively form an actuation shaft assembly. Rotation of the adjustment knob 220 relative to the actuation shaft 234 can adjust the effective length of the assembly as measured along the axis A1, and thereby adjust the amount of tension applied to the wire 212 when the handle assembly 202 is actuated. The adjustment knob 220 can include a wheel 238 that protrudes above an exterior surface of the handle frame 214 such that the knob can be rotated by a user. The wheel 238 can be knurled or can include other gripping features to facilitate such rotation. The wheel 238 can define a distal-facing shoulder. A flange 240 can be formed at the distal end of the adjustment knob 220 to define a proximal-facing shoulder. The plate 228 can include one or more protrusions 242 disposed between the proximal and distal facing shoulders of the adjustment knob 220. Accordingly, translation of the adjustment knob 220 along the axis A1 can be transferred to the plate 228, while still allowing free rotation of the adjustment knob relative to the plate. The plate 228 can include first and second opposed protrusions 242 as shown that define a seat therebetween for receiving the adjustment knob 220.

In operation, movement of the handle levers 216 towards one another can cause the linkage bar 236 to pivot relative to the handle levers. The linkage bar 236 can have a fixed length, such that said pivoting causes the actuation shaft 234 to translate longitudinally along the axis A1 in a proximal direction relative to the handle frame 214. This movement of the actuation shaft 234 can impart corresponding movement to the adjustment knob 220, plate 228, and tension pulley 218, thereby increasing the tension applied to the wire 212 of the arm assembly 204. Movement of the handle levers 216 away from one another can impart opposite movement of the components, translating the tension pulley 218 distally along the axis A1 to decrease the tension applied to the wire 212 of the arm assembly 204. The adjustment knob 220 can be rotated relative to the handle frame 214 about the axis A1 to adjust the tension that is applied to the wire 212. Rotating the adjustment knob 220 in a first direction can be effective to thread the actuation shaft 234 deeper into the adjustment knob, shortening the overall length of the assembly and moving the tension pulley 218 proximally to increase the tension applied to the wire 212. Rotating the adjustment knob 220 in a second, opposite direction can be effective to unthread the actuation shaft 234 from the adjustment knob, lengthening the assembly and moving the tension pulley 218 distally to decrease the tension applied to the wire 212.

The handle assembly 202 can include a locking mechanism for selectively maintaining the handle assembly in the open and/or closed configurations. The locking mechanism can be active while the handle assembly 202 is in the open configuration to lock the handle assembly in the open configuration. The locking mechanism can be active while the handle assembly 202 is in the closed configuration to lock the handle assembly in the closed configuration.

For example, as shown in the illustrated embodiment, the linkage bar 236 can be mounted to the handle levers 216 to achieve an over-center action, in a manner similar to locking pliers, thereby forming a locking mechanism that is active in the closed configuration. As the handle levers 216 are moved towards one another, the linkage bar 236 and the movable handle 216B can enter an over-center condition, locking the handle levers in the closed position. In particular, the angle A shown in FIG. 2D can approach and then exceed 180 degrees as the assembly enters the over-center condition. The handle assembly 202 can include a release lever 244 for moving the assembly out of the over-center condition. The release lever 244 can be pivotally mounted to the movable handle lever 216B. Rotation of the distal end of the release lever 244 towards the movable handle lever 216B can urge a bearing surface 246 of the lever against the linkage bar 236, prying the movable handle lever away from the linkage bar and the fixed handle lever 216A, thereby providing mechanical advantage to the user in moving the handle levers apart. As the handle levers 216 are spread apart, they can move the assembly out of the over-center condition to unlock the connector 200.

Figure 2E:
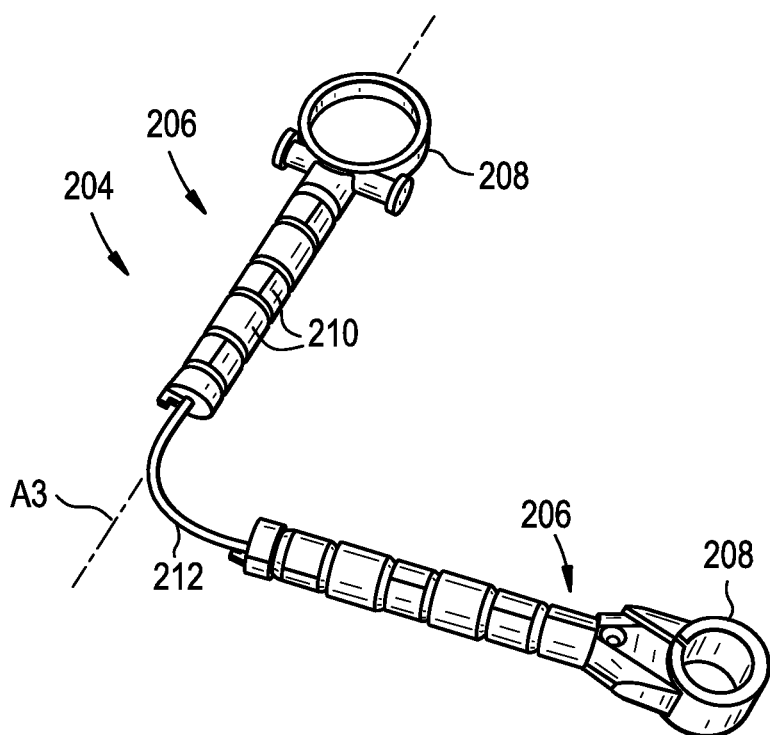
FIG. 2E is a perspective view of an arm assembly of the connector of FIG. 2A.
Figure 2F:
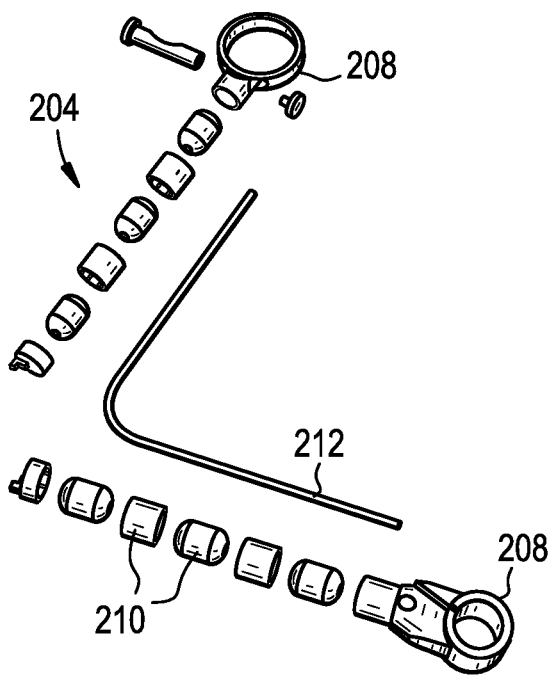
FIG. 2F is an exploded perspective view of the arm assembly of FIG. 2E.
Figure 2G:
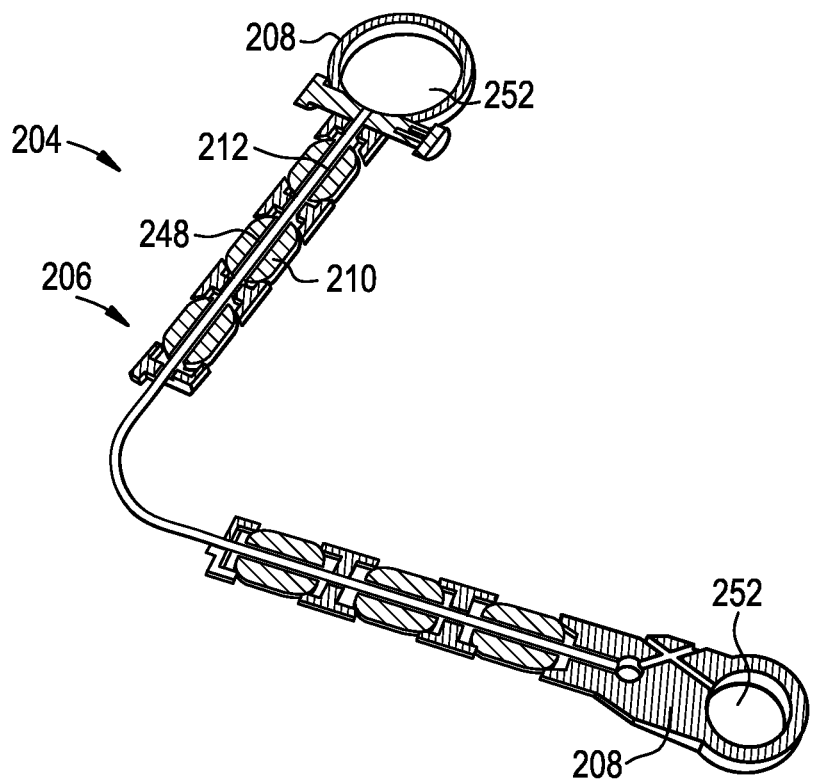
FIG. 2G is a sectional perspective view of the arm assembly of FIG. 2E.

The arm assembly 204 is shown in greater detail in FIGS. 2E-2G. The arm assembly 204 can include at least one arm 206, e.g., first and second arms as shown. The arm 206 can include a plurality of nested segments 210 disposed end-to-end along a neutral axis A3 of the arm. An actuation wire 212 can extend through the segments 210. An attachment feature 208 can be disposed on the arm 206, e.g., at a distal free end of the arm. When tension on the wire 212 is reduced, the segments 210 can be movable with respect to one another in one or more degrees of freedom. For example, in the illustrated arrangement, the segments 210 can pitch, yaw, and roll with respect to one another when the tension on the wire 212 is reduced. In other arrangements, the segments 210 can be movable in fewer degrees of freedom or in additional degrees of freedom. When tension on the wire 212 is increased, the segments 210 can be pulled into firm engagement with one another, resisting or preventing relative movement therebetween. The wire 212 can also be configured to control the attachment feature 208, e.g., such that tension applied to the wire is effective to open or close the attachment feature, or to otherwise connect or disconnect the attachment feature from an attached object. In some embodiments, a single wire 212 can be used to lock and unlock a plurality of arms 206 of the connector 200 and to actuate a plurality of attachment features 208 of the connector. In some embodiments, each arm of the connector can include an independent wire for locking and unlocking said arm and for actuating an attachment feature of said arm. In some embodiments, a single wire can be used to lock and unlock a plurality of arms of the connector and a separate single wire can be used to actuate a plurality of attachment features of the connector.

The plurality of nested segments 210 of each arm 206 can include a proximal-most segment and a distal-most segment. The plurality of nested segments 210 can include one or more intermediate segments disposed between the proximal-most and distal-most segments. The proximal-most segment can include a distal bearing surface that contacts an adjacent segment and a proximal bearing surface that contacts a branch 222 of the handle frame 214. The proximal-most segment can alternatively be attached to the handle frame 214 or formed integrally with the handle frame. The distal-most segment can include a proximal bearing surface that contacts an adjacent segment and a distal bearing surface that contacts an attachment feature 208. The distal-most segment can alternatively be attached to the attachment feature 208 or formed integrally with the attachment feature. Each intermediate segment can include proximal and distal bearing surfaces that contact and bear against counterpart bearing surfaces of adjacent segments.

Each segment 210 can include an inner passage or cannulation 248 through which the wire 212 extends. The inner passage 248 can be cylindrical or substantially cylindrical. The inner passage 248 can have a diameter that is only slightly greater than or equal to the outside diameter of the wire 212. The inner passage 248 can have conical or otherwise-flared sections at the proximal and distal ends thereof to provide a relief for bending of the wire 212 as the arm 206 is articulated.

Figure 3A:
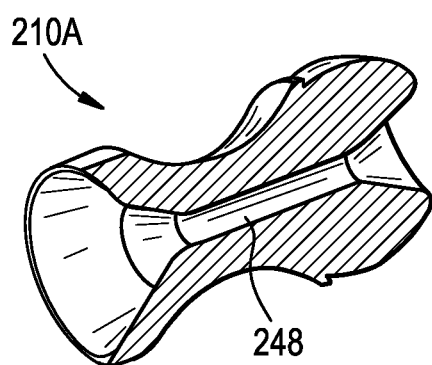
FIG. 3A is a sectional perspective view of a segment that can be used in the connectors herein.
Figure 3B:
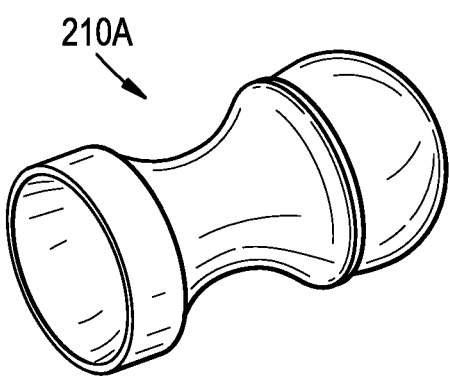
FIG. 3B is a perspective view of the segment of FIG. 3A.
Figure 3C:
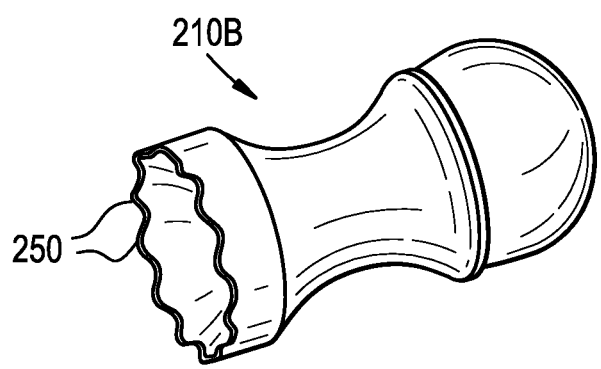
FIG. 3C is a perspective view of another segment that can be used in the connectors herein.

It will be appreciated that the segments 210, and the bearing surfaces thereof, can have any of a variety of geometries. In FIG. 2F, for example, each arm 206 includes alternating male and female segments 210, with the male segments having proximal and distal male bearing surfaces and the female segments having proximal and distal female bearing surfaces. In other arrangements, each segment can have one male bearing surface and one female bearing surface. As shown in FIGS. 3A-3B, a segment 210A can include a spherical male bearing surface at one end (e.g., a distal end or a proximal end) and a spherical female bearing surface at the other end (e.g., a proximal end or a distal end). The segment 210A can include a cylindrical inner passage 248 with opposed conical end sections. As shown in FIG. 3C, a segment 210B can include a ring-shaped terminal end surface that defines a plurality of teeth 250 for enhancing grip with an adjacent segment. A segment 210 can include a cylindrical bearing surface, e.g., to limit articulation with an adjacent segment to uniplanar movement. A segment 210 can include rotation stops to limit the degree to which the segment can rotate relative to an adjacent segment.

The segments 210 of the arm assembly 204 can include various features for providing increased friction while maintaining a broad range of motion. For example, the segment 210 can include features that lead to a form fit by deforming one or both of two adjacent segments. A segment can be formed with a relatively hard material at the edge of the concave part of the segment and can be paired with a segment having a more deformable material at the convex part. A segment can include two different materials having different hardness. A segment can include cut-outs that increase the sharpness of the edge of the concave part of the segment. A segment can include ripples or small extrusions or other surface features in the concave and/or convex part of the segment, with the counterpart including a more deformable material.

The segment can include features that increase the friction coefficient with adjacent segments. For example, one or both counterpart mating surfaces of the segments can be bead-blasted or formed from a material with a high coefficient of friction.

The arm assembly 204 can include any of a variety of attachment features 208. The attachment feature 208 can define a central opening 252 through which an object, e.g., a surgical instrument, can be received. The attachment feature 208 can be positioned in a "closed" state, in which the attachment feature is locked to an object disposed therein to resist or prevent relative movement between the attachment feature and the object. The attachment feature 208 can be positioned in an "open" state, in which the attachment feature is not locked to an object disposed therein and in which the object can be removed from the attachment feature and/or moved in one or more degrees of freedom with respect to the attachment feature. The attachment feature 208 can have resilient properties. The attachment feature 208 can be configured to provide a pre-load or provisional friction fit to an object received therein prior to locking the attachment feature. The attachment features described herein can be used in any combination. All arms of the connector can include the same type of attachment feature, or one or more arms can include an attachment feature that differs from the attachment feature of one or more other arms.

Figure 4A:
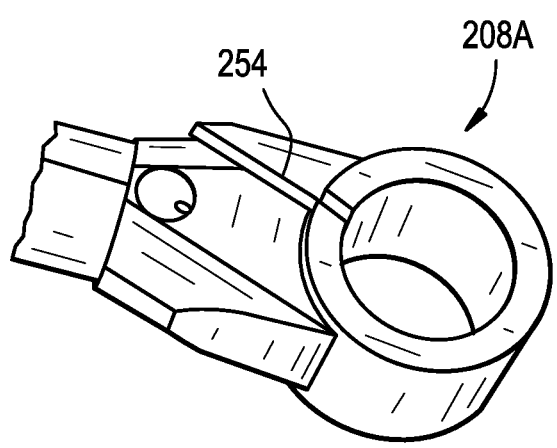
FIG. 4A is a perspective view of an attachment feature that can be used in the connectors herein.

FIG. 4A illustrates a ring clamp attachment feature 208A. The attachment feature 208A can include a generally cylindrical body with a slit 254 formed therein to allow radial expansion and/or radial contraction of the body. The wire 212 can extend across the slit 254 such that tension applied to the wire pulls opposed sidewalls of the slit towards one another to close the attachment feature 208A and clamp down on an object inserted therethrough. When tension is released from the wire 212, resilient material properties of the body can cause the opposed sidewalls of the slit 254 to move away from one another towards their resting state, releasing the attachment feature 208A from an object disposed therein. The wire 212 can extend through opposed proximal wings of the attachment feature 208A.

Figure 4B:
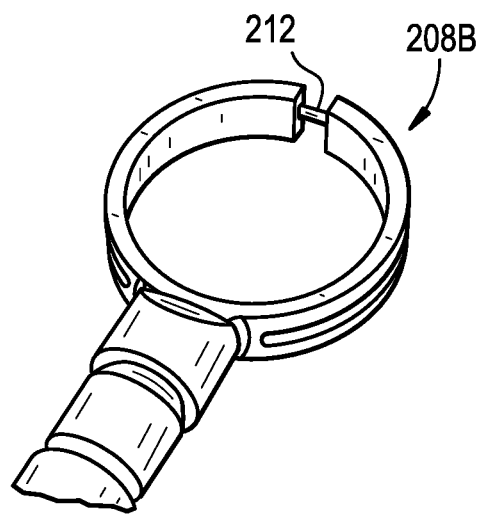
FIG. 4B is a perspective view of another attachment feature that can be used in the connectors herein.

FIG. 4B illustrates another ring clamp attachment feature 208B. The attachment feature 208B is substantially the same as that of FIG. 4A, except that the wire 212 extends around the circumference of the body.

Figure 4C:
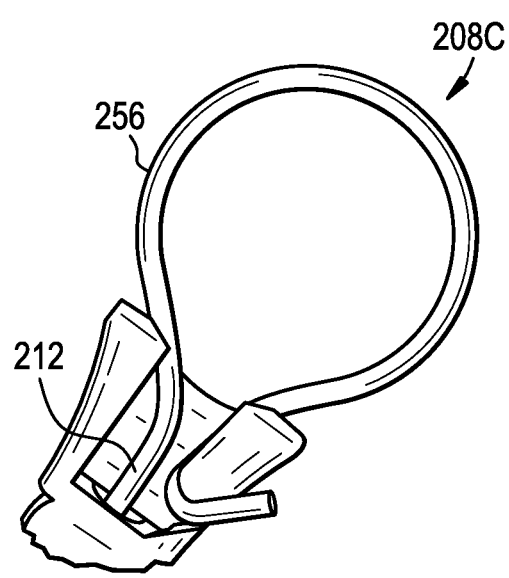
FIG. 4C is a perspective view of another attachment feature that can be used in the connectors herein.

FIG. 4C illustrates a lasso attachment feature 208C. The attachment feature 208C can include a loop of wire 256 through which an instrument or other object can be inserted. The loop of wire 256 can be an integral extension of the actuation wire 212 of the arm assembly 204 as shown. The free end of the wire 212 can be fixed at a termination of the attachment feature 208C, such that application of tension to the wire 212 can be effective to reduce the diameter of the loop 256, thereby clamping onto an object disposed therethrough.

Figure 4D:
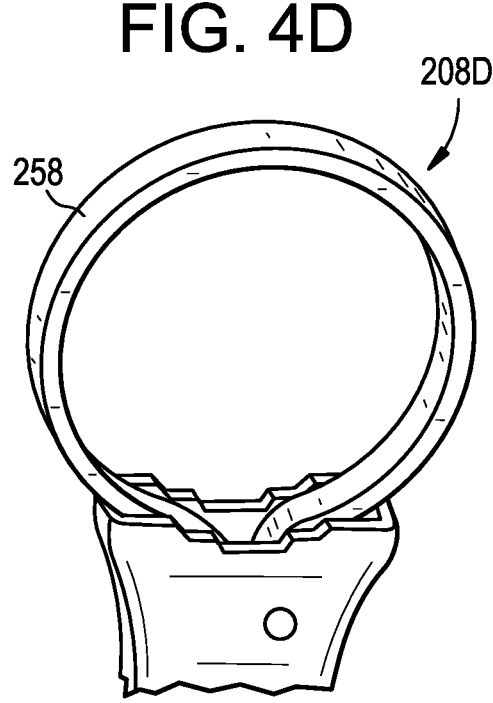
FIG. 4D is a perspective view of another attachment feature that can be used in the connectors herein.

FIG. 4D illustrates another lasso attachment feature 208D. The attachment feature 208D can include a looped member 258 having an increased aspect ratio. For example, the member 258 can have a height dimension that is greater than a radial thickness of the looped member. The looped member 258 can be a cylindrical tube with square cut ends. The looped member 258 can have a rectangular transverse cross-section. The looped member 258 can be an integral extension of the actuation wire 212 of the arm assembly 204, or can be attached thereto. Application of tension to the wire 212 can be effective to reduce the diameter of the looped member 258, thereby clamping onto an object disposed therethrough. Lasso attachment features can be more forgiving if the tension applied to the wire 212 is sub-optimal, if the instrument or object being clamped is non-circular, etc.

Figure 4E:
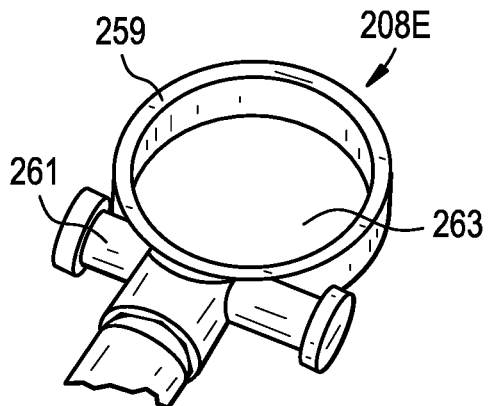
FIG. 4E is a perspective view of another attachment feature that can be used in the connectors herein.

FIG. 4E illustrates another attachment feature 208E. The attachment feature 208E can include a closed ring 259 and a locking bar 261. At least a portion of the bar 261 can intersect a central opening 263 of the ring 259. Movement of the bar 261 relative to the ring 259 can be effective to adjust the cross-sectional area of the central opening 263, e.g., by changing the degree to which the bar protrudes into the opening or by aligning or misaligning a cut-out formed in the bar with the opening. For example, rotating the bar 261 about its axis in a first direction can increase the cross-sectional area of the opening 263, e.g., to release an instrument or object inserted therethrough, and rotating the bar about its axis in a second, opposite direction can decrease the cross-sectional area of the opening, e.g., to clamp onto an instrument or object inserted therethrough. To achieve this function, the bar 261 can have a radial thickness that varies about its circumference. As another example, sliding the bar 261 along its axis in a first direction can increase the cross-sectional area of the opening 263, e.g., to release an instrument or object inserted therethrough, and sliding the bar along its axis in a second, opposite direction can decrease the cross-sectional area of the opening, e.g., to clamp onto an instrument or object inserted therethrough. To achieve this function, the bar 261 can have a radial thickness that varies along its length, or can have a ramp-shaped protrusion along a surface of the bar that protrudes into the central opening 263. For example, the bar 261 can be conically shaped with a relatively larger diameter at one end and a relatively smaller diameter at the other end with a tapered sidewall extending therebetween. The bar 261 can clamp to an instrument or object inserted through the opening 263 via self-retaining friction, via form-fit, or via a combination of both. The bar 261 can include a cut-out or recess that, when aligned with the opening 263, allows an instrument or object to be inserted through the opening. The instrument or object can include a cut-out or recess that receives the bar 261 after the bar is moved relative to the ring 259 to positively interlock the bar with the instrument or object and thereby retain the instrument or object within the attachment feature 208E. The instrument or object can include a plurality of incremental cut-outs, e.g., spaced along a length and/or circumference of the instrument or object.

Figure 4F:
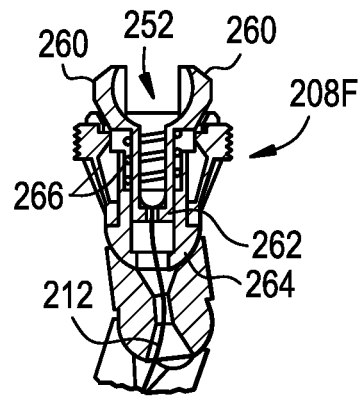
FIG. 4F is a sectional plan view of another attachment feature that can be used in the connectors herein.
Figure 4G:
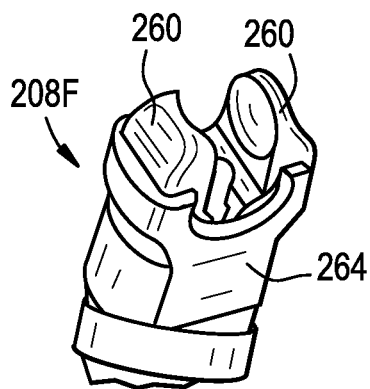
FIG. 4G is a perspective view of the attachment feature of FIG. 4F.

FIG. 4F-4G illustrate a jaw-type attachment feature 208F. The attachment feature 208F can include first and second opposed jaws 260 that define an instrument channel 252 therebetween in which an instrument can be disposed. The jaws 260 can be movable towards and away from one another. For example, the jaws 260 can be opposed cantilevered sections of a main jaw body 262 that are bendable towards and away from one another. Resilient material properties of the jaws 260 can be effective to bias the jaws apart from one another towards a resting position. The jaws 260 can be slidably mounted in an actuation sleeve 264. The actuation sleeve 264 and/or the jaws 260 can include ramp or wedge surfaces that contact and bear against one another. Accordingly, proximal translation of the jaws 260 relative to the sleeve 264 can cause the jaws to move towards one another, and distal translation of the jaws relative to the sleeve can cause the jaws to move apart from one another. The jaws 260 can be biased distally relative to the sleeve 264 by a spring 266. The sleeve 264 can be maintained at a fixed longitudinal position at the end of the arm 206, and the jaw body 262 can be coupled to the wire 212 of the arm assembly 204. In use, tension can be applied to the wire 212 to pull the jaw body 262 proximally relative to the sleeve 264, closing the jaws 260 together to clamp onto an instrument disposed therebetween. When tension on the wire is relaxed, the jaw body 262 can move distally relative to the sleeve 264 under the bias of the spring 266 and/or the resilient material properties of the jaws 260, opening the jaws apart from one another to release an instrument disposed therebetween. As shown in FIG. 4G, inner surfaces of the jaws 260 can include a depression having a geometry that corresponds to that of an object to be grasped by the jaws. For example, the jaws 260 can include a spherical depression for grasping onto a spherical attachment feature of an instrument, or a cylindrical depression for grasping onto a cylindrical access device or other instrument.

Figure 4H:
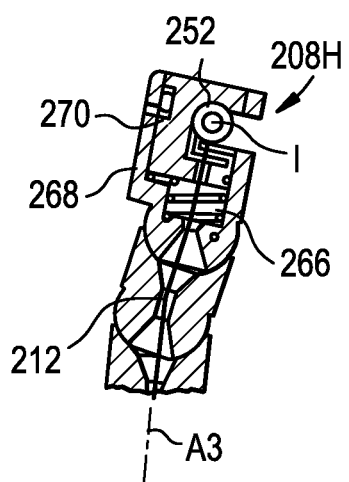
FIG. 4H is a sectional plan view of another attachment feature that can be used in the connectors herein.

FIG. 4H illustrates a side-loading jaw-type attachment feature 208H. The attachment feature 208H can include a sleeve 268 and a movable jaw 270 that collectively define an instrument channel or slot 252. The instrument channel 252 can be open in a lateral direction, such that an instrument I can be introduced into the channel by moving the instrument perpendicular or substantially perpendicular to the axis A3. When tension is applied to the wire 212, the movable jaw 270 can be pulled proximally to clamp an instrument between the jaw and the sleeve 268. When tension is released from the wire 212, the movable jaw 270 can be urged distally under the bias of a spring 266 to release an instrument from between the jaw and the sleeve 268.

Figure 4I:
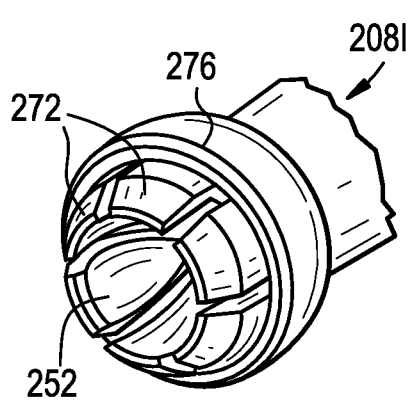
FIG. 4I is a perspective view of another attachment feature that can be used in the connectors herein.
Figure 4J:
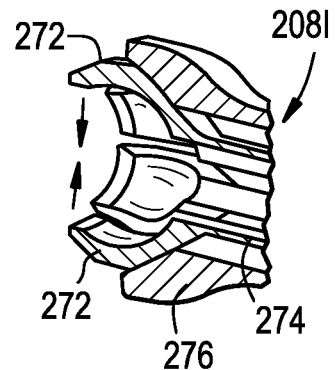
FIG. 4J is a sectional perspective view of the attachment feature of FIG. 4I.

FIGS. 4I-4J illustrate a spherical clamp attachment feature 208I. The attachment feature 208I can include a plurality of jaws 272 (e.g., six jaws as shown) that collectively define a cavity 252 in which an instrument or an attachment feature of an instrument can be disposed. The cavity 252 can be spherical and can be configured to receive a spherical instrument attachment feature. The jaws 272 can be movable towards and away from one another, e.g., to decrease or increase the diameter of a spherical cavity 252 defined therebetween. For example, the jaws 272 can be formed by cantilevered sections of a main jaw body 274 that are bendable towards and away from one another. Resilient material properties of the jaws 272 can be effective to bias the jaws apart from one another towards a resting position. The jaws 272 can be slidably mounted in an actuation sleeve or bowl 276. The actuation sleeve 276 can include ramp or wedge surfaces that contact and bear against corresponding ramp or wedge surfaces of the jaws 272. Accordingly, proximal translation of the jaws 272 relative to the sleeve 276 can cause the jaws to move towards one another, and distal translation of the jaws relative to the sleeve can cause the jaws to move apart from one another. The jaws 272 can be biased distally relative to the sleeve 276 by a spring. The sleeve 276 can be maintained at a fixed longitudinal position at the end of the arm 206, and the jaw body 274 can be coupled to the wire 212 of the arm assembly 204. In use, tension can be applied to the wire 212 to pull the jaw body 274 proximally relative to the sleeve 276, closing the jaws 272 together to clamp onto an instrument disposed therebetween. When tension on the wire 212 is relaxed, the jaw body 274 can move distally relative to the sleeve 276 under the bias of the spring and/or the resilient material properties of the jaws 272, opening the jaws apart from one another to release an instrument disposed therebetween.

The connectors disclosed herein can be biased towards an open or unlocked position, and user input force can be required to move the connector to a closed or locked position. Alternatively, the connectors disclosed herein can be biased towards a closed or locked position, and user input force can be required to move the connector to an open or unlocked position. In the handle assembly 202 described above, the pulley 218 is biased distally by the tension in the wire 212, such that the connector 200 is biased towards an open position.

Figure 5A:
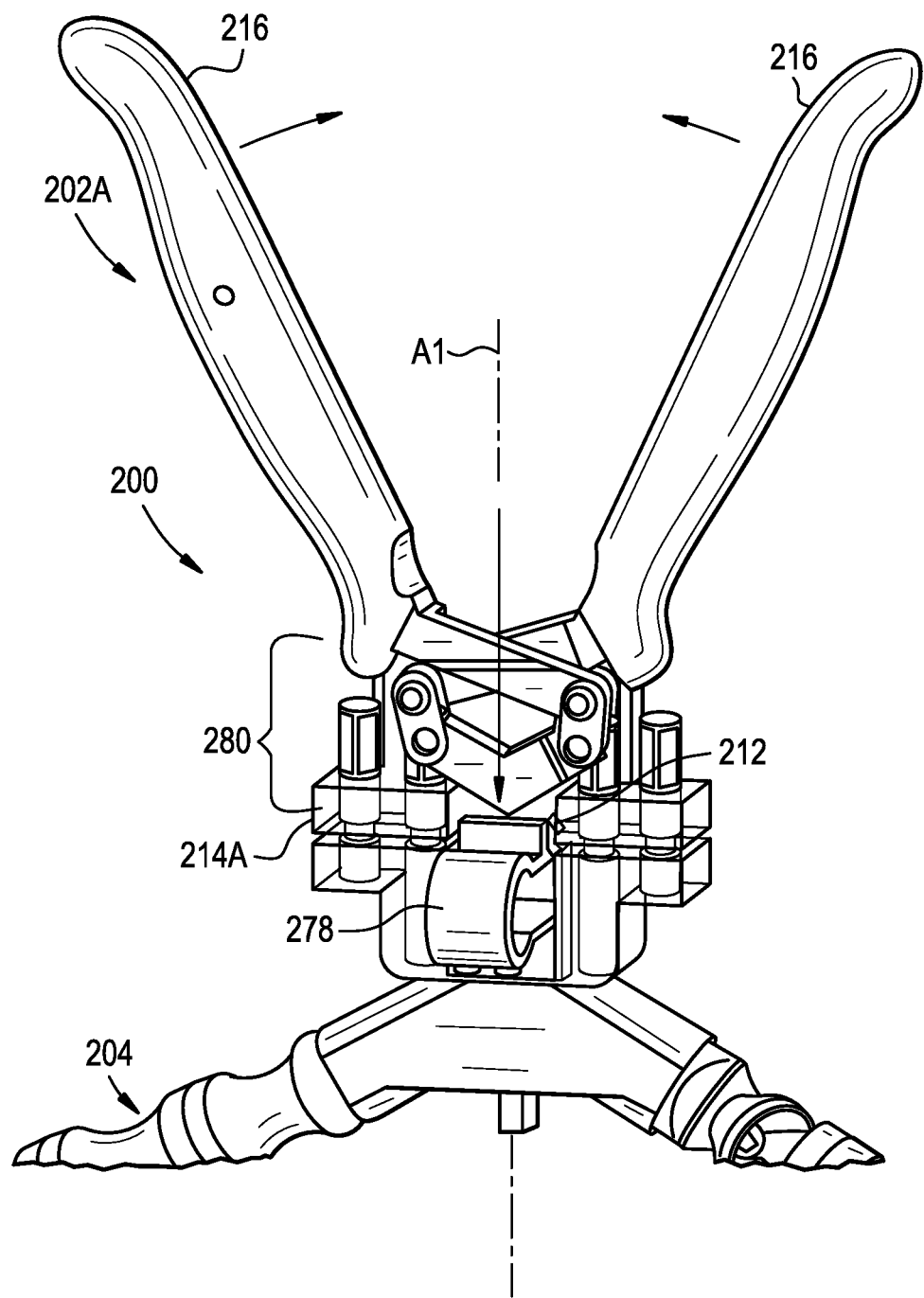
FIG. 5A is a perspective view of the connector of FIG. 2A, shown with an alternate handle assembly.

FIG. 5A illustrates an alternative handle assembly 202A that can be used with the connector 200 in which the connector is biased towards a closed position. The handle assembly 202A can include a spring element 278 mounted to the handle frame 214A. For example, the handle assembly 202A can include a C-spring, band, or plate spring 278 as shown. The wire 212 of the arm assembly 204 can extend around the spring element 278, such that the bias of the spring element 278 exerts tension on the wire. When no user input force is applied to the handle levers 216, the arms of the C-spring 278 can tend to move apart from one another, pushing the wire 212 proximally relative to the handle frame 214 to apply tension to the wire. When the handle levers 216 are moved towards one another, the spring element 278 can be compressed to allow the wire 212 to move distally relative to the handle frame 214 to relax the tension on the wire. For example, the handle levers 216 can be pivotally coupled to a scissor linkage 280 that acts against the spring 278. Movement of the handle levers 216 towards one another as shown by the illustrated arrows can expand the scissor linkage 280 along the axis A1, compressing the spring 278 to release tension from the wire 212. Movement of the handle levers 216 away from one another can contract the scissor linkage 280 along the axis A1, allowing the spring 278 to expand and exert tension on the wire 212. The spring force of the spring 278 can be effective to bias the handles 216 apart from one another. In use, a user can easily unlock, reposition, and relock the connector 200 by squeezing the handle levers 216 together, articulating or moving the arms 206 of the connector 200 and/or the instruments or objects attached thereto, and then releasing the handle levers.

Figure 5B:
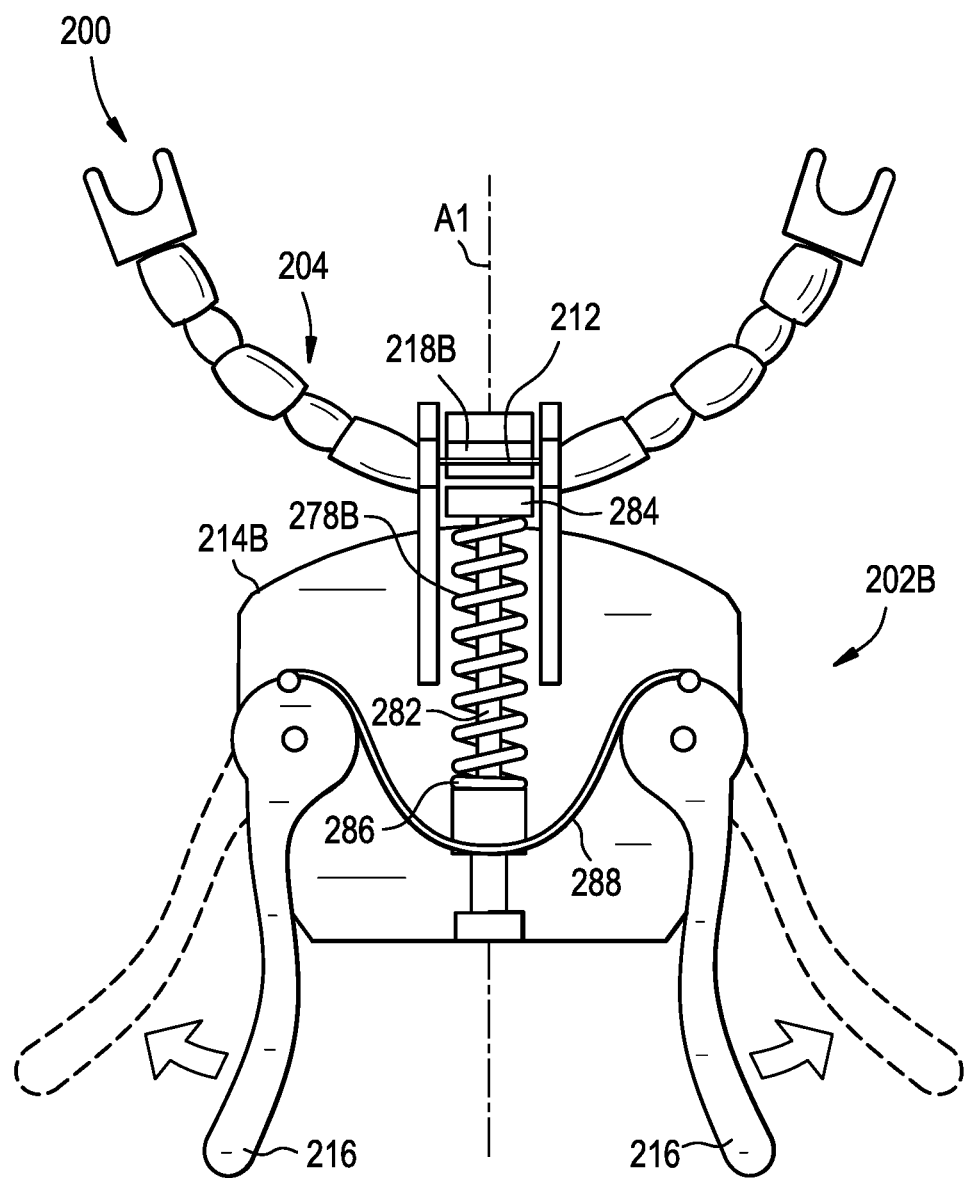
FIG. 5B is a perspective view of the connector of FIG. 2A, shown with another alternate handle assembly.

FIG. 5B illustrates another exemplary handle assembly 202B that can be used with the connector 200 in which the connector is biased towards a closed position. The handle assembly 202B can include a tension head 218B slidably mounted to the handle frame 214B. The tension head 218B can be movable along the axis A1 to increase or decrease the tension on the wire 212. Distal movement of the tension head 218B relative to the frame 214B can decrease the tension on the wire 212 and proximal movement of the tension head relative to the frame can increase the tension on the wire. The tension head 218B can include a shaft 282 that extends along the axis A1. A spring 278B can be disposed between a shoulder 286 formed on the shaft 282 and a spring seat 284 fixed to the handle frame 214B. The spring 278B can be effective to bias the shoulder 286 away from the spring seat 284, thereby biasing the tension head 218B in a proximal direction in which it applies increased tension to the wire 212. The handle assembly 202B can include first and second movable handle levers 216. Movement of the handle levers 216 towards one another can move the shoulder 286 distally, and by extension can move the shaft 282 and the tension head 218B distally to compress the spring 278B and relax the tension on the wire 212. Various mechanisms can be used to convert movement of the handles 216 towards one another into distal movement of the shoulder 286. For example, as shown, the handle levers 216 can be linked by a flexible tether 288 that is attached at its free ends to respective fixed points along a curved protrusion of the handle levers. The shoulder 286 can be supported at a midpoint of the tether 288. As the handle levers 216 move towards one another, the tether 288 can wind onto the curved portions of the handle levers, reducing the slack in the tether and moving the shoulder 286 distally. As the handle levers 216 move away from one another, the tether 288 can unwind from the curved portions of the handle levers, increasing the slack in the tether and allowing the shoulder 286 to move proximally under the bias of the spring 278B. In use, a user can easily unlock, reposition, and relock the connector 200 by squeezing the handle levers 216 together, articulating or moving the arms 206 of the connector 200 and/or the instruments or objects attached thereto, and then releasing the handle levers.

Figure 5C:
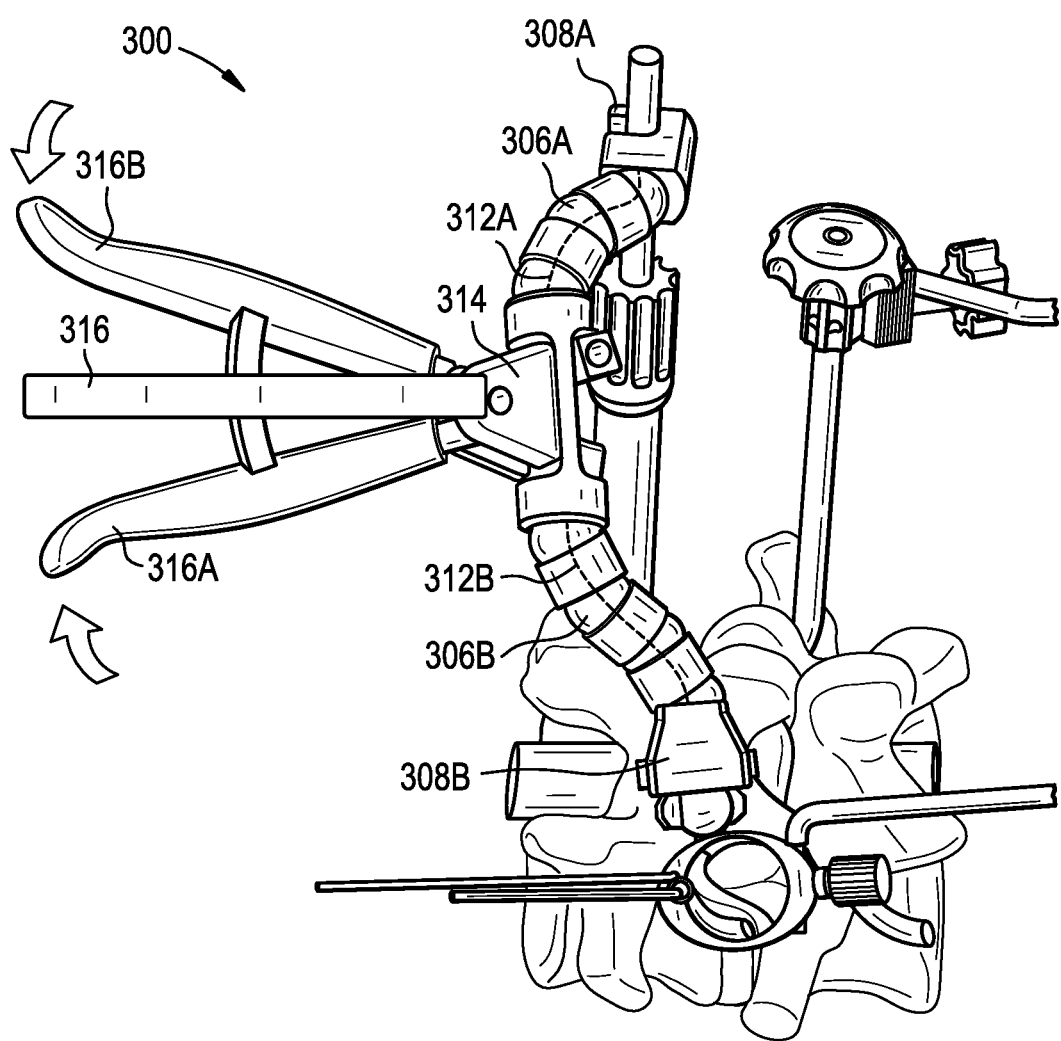
FIG. 5C is a perspective view of another connector.

The connector can include one or more arms that can be selectively locked or unlocked independently of one another. For example, FIG. 5C illustrates a connector 300 having first and second arms 306A, 306B coupled to a handle frame 314 having a fixed handle lever 316 and first and second movable handle levers 316A, 316B. Each arm 306A, 306B can include its own independent actuation wire 312A, 312B. In use, moving the first movable handle lever 316A towards the fixed handle lever 316 can apply tension to the first wire 312A to lock the first arm 306A and/or an attachment feature 308A thereof. In particular, rotation of the first handle lever 316A about a first pivot point can move the distal end of the first handle lever away from the proximal end of the first arm 306A to tension the first wire 312A. Movement of the second movable handle lever 316B towards the fixed handle lever 316 can apply tension to the second wire 312B to lock the second arm 306B and/or an attachment feature 308B thereof. In particular, rotation of the second handle lever 316B about a second pivot point can move the distal end of the second handle lever away from the proximal end of the second arm 306B to tension the second wire 312B. The first and second movable handle levers 316A, 316B can be independently movable, such that the first and second arms 306A, 306B can be locked or unlocked independently and/or such that the first and second attachment features 308A, 308B can be locked or unlocked independently. The fixed handle lever 316 can serve as a datum or foundation and the movable handle levers 316A, 316B can be independently-movable with respect thereto to allow for independent locking of each arm 306. The arms 306 and the attachment features 308 can include any of the features described herein. In other arrangements, movement of the handle levers can be effective to independently unlock the arms 306 and/or the attachment features 308.

Figure 5D:
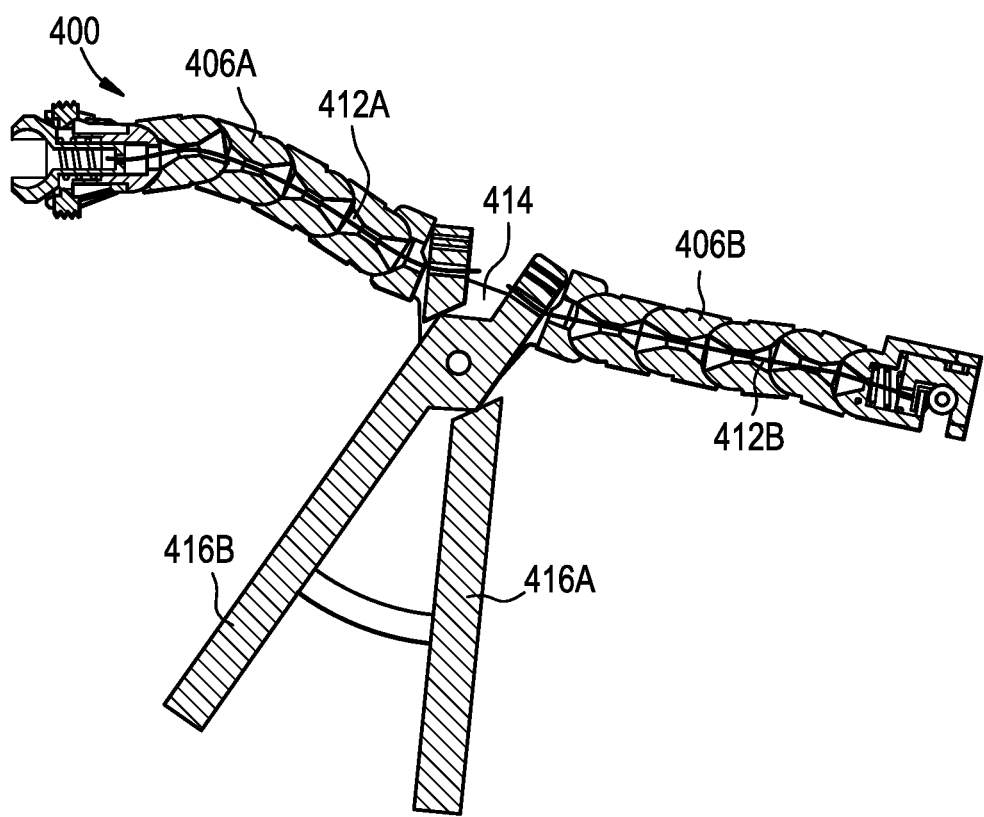
FIG. 5D is a sectional perspective view of another connector.

FIG. 5D illustrates a connector 400 similar to that of FIG. 5C except that the fixed handle lever is omitted. The connector 400 can include a handle frame 414 having first and second handle levers 416A, 416B coupled to respective first and second wires 412A, 412B of respective first and second arms 406A, 406B to selectively and/or independently apply tension thereto.

Figure 6A:
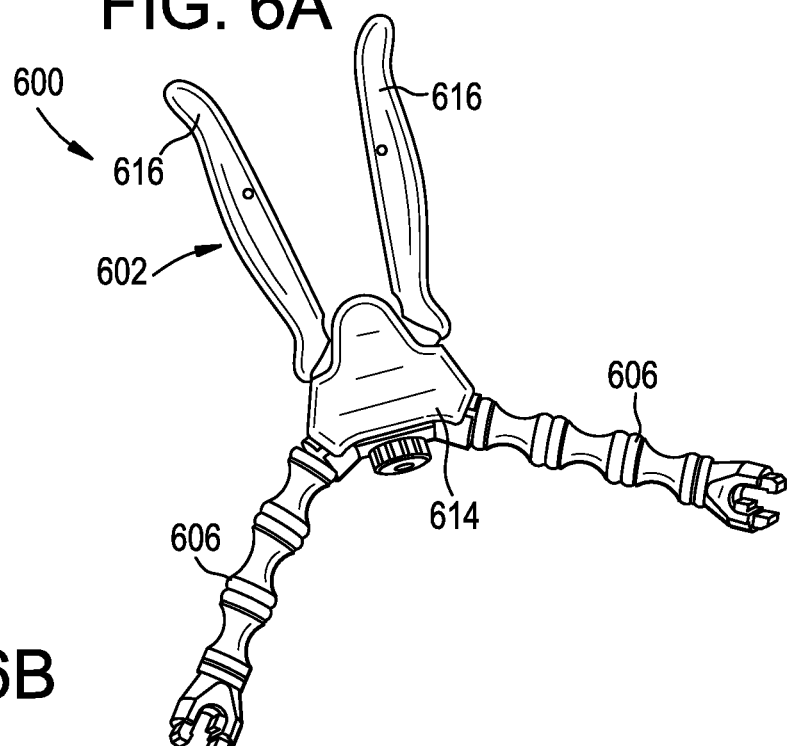
FIG. 6A is a perspective view of another connector.
Figure 6B:
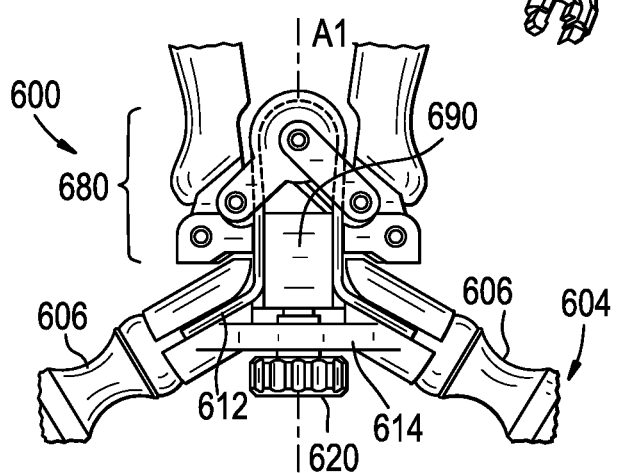
FIG. 6B is a perspective detail view of the connector of FIG. 6A in a locked configuration.
Figure 6C:
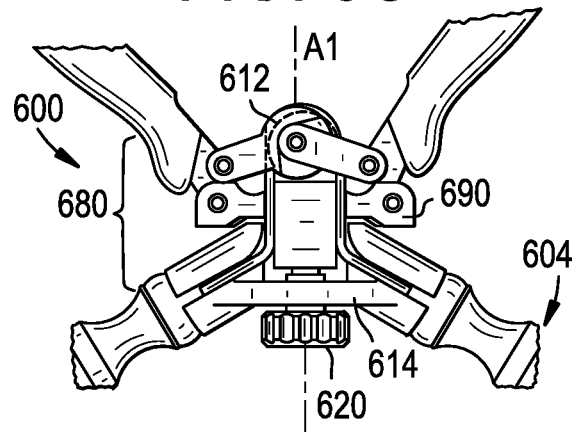
FIG. 6C is a perspective detail view of the connector of FIG. 6A in an unlocked configuration.

FIGS. 6A-6C illustrate another exemplary connector 600 that can be used to connect a first object to a second object. For example, the connector 600 can be used to connect first and second surgical instruments. By way of further example, the connector 600 can be used in the system 100 described above, e.g., to connect the access device 102 to the support or anchor 106. Except as indicated below and as will be readily appreciated by a person having ordinary skill in the art in view of the present disclosure, the structure and operation of the connector 600 is substantially the same as that of the connector 200 described above.

The connector 600 can include a tension pulley 618 mounted to the handle frame 614 by a scissor linkage 680. The connector 600 can include first and second movable handle levers 616. As shown in FIG. 6B, pivoting the handle levers 616 towards one another can expand the height of the scissor linkage 680 along the axis A1, moving the tension pulley 618 proximally to apply tension to the actuation wire 612 of the arm assembly 604. As shown in FIG. 6C, pivoting the handle levers 616 away from one another can reduce the height of the scissor linkage 680 along the axis A1, moving the tension pulley 618 distally to relax the tension on the actuation wire 612 of the arm assembly 604. The scissor linkage 680 can provide mechanical advantage, multiplying the user input force applied to the handle levers 616 to provide a relatively high locking force on the connector 600 in response to a relatively low input force.

The scissor linkage 680 can be mounted to the handle frame 614 by a slidable body 690 to which the handle levers 616 are pivotally coupled. The body 690 can be connected to the handle frame 614 by a threaded adjustment screw 620. Rotation of the screw 620 in a first direction can be effective to shift the body 690 proximally relative to the handle frame 614, increasing the preload tension applied by the handle assembly 602. Rotation of the screw 620 in a second, opposite direction can be effective to shift the body 690 distally relative to the handle frame 614, decreasing the preload tension applied by the handle assembly 602.

Figure 7A:
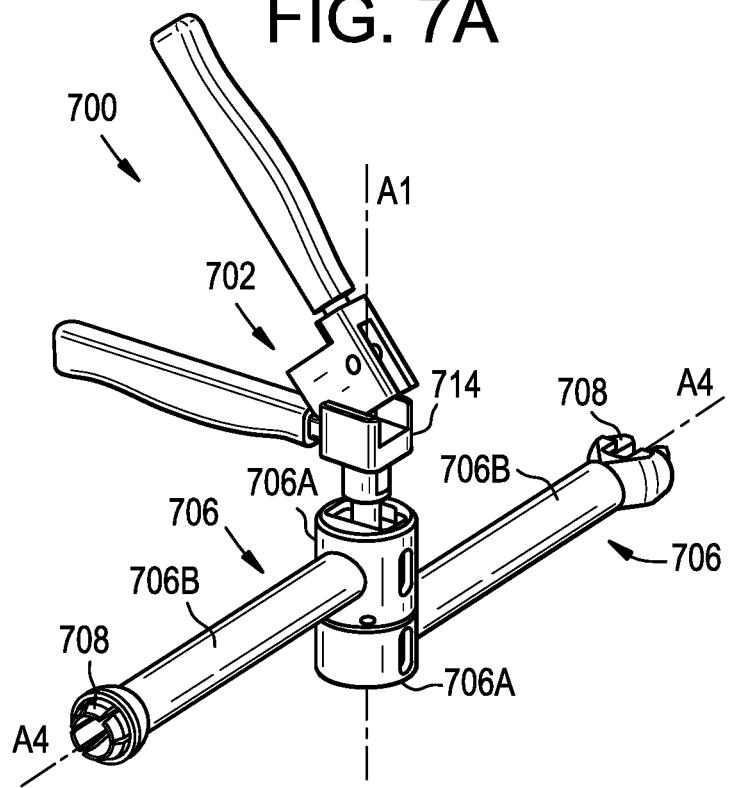
FIG. 7A is a perspective view of another connector, shown in an unlocked configuration.
Figure 7B:
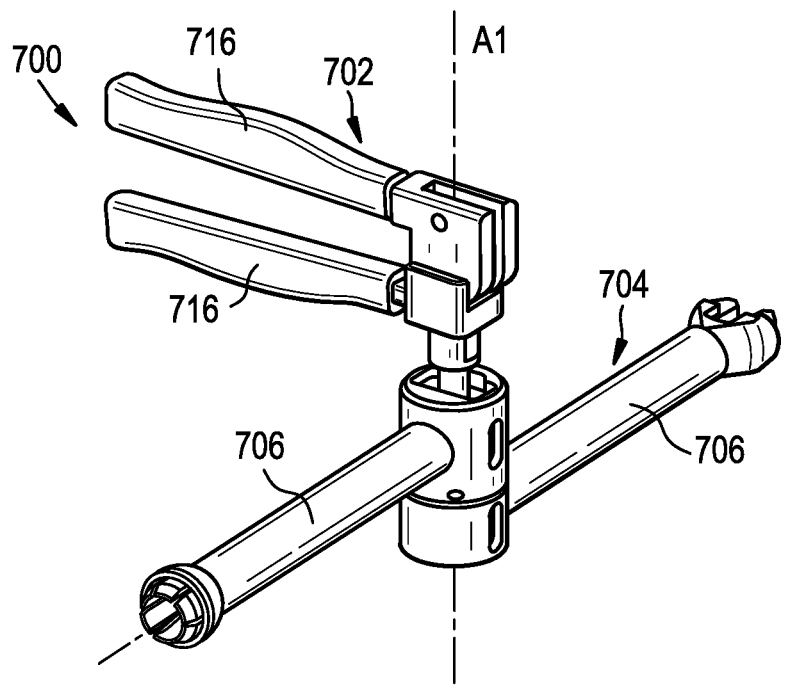
FIG. 7B is a perspective view of the connector of FIG. 7A in a locked configuration.

FIGS. 7A-7C illustrate another exemplary connector 700 that can be used to connect a first object to a second object. For example, the connector 700 can be used to connect first and second surgical instruments. By way of further example, the connector can be used in the system 100 described above, e.g., to connect the access device 102 to the support or anchor 106. Except as indicated below and as will be readily appreciated by a person having ordinary skill in the art in view of the present disclosure, the structure and operation of the connector 700 is substantially the same as that of the connector 200 described above.

The connector 700 can include one or more arms 706. The arms 706 can be rotatable relative to one another about the axis A1. The arms 706 can be rotatable relative to the handle frame 714 about the axis A1. Each arm 706 can include a first tubular portion 706A that extends along the axis A1 and a second tubular portion 706B that extends along a respective axis A4 that is perpendicular or obliquely angled relative to the axis A1. Each arm 706 can include a clamp 708 slidably mounted therein. An actuation shaft 734 can extend through the first tubular portions 706A of each arm and can connect the arms 706 to a handle assembly 702. The actuation shaft 734 can be coupled to the clamps 708 such that translation of the actuation shaft along the axis A1 causes translation of the clamps along their respective axes A4. In the illustrated arrangement, proximal translation of the actuation shaft 734 pulls the clamps 708 inward towards the axis A1, causing the outer tubular portions 706B of the arms 706 to compress the clamp 708 jaws inward onto an instrument or other object disposed therein. Proximal movement of the actuation shaft 734 can also pull the first tubular portions 706A of the arms 706 towards one another to lock relative rotation between the arms about the axis A1.

Distal translation of the actuation shaft 734 pushes the clamps 708 outward away from the axis A1, moving the clamp 708 jaws away from the outer tubular portions 706B of the arms 706, allowing the jaws to open to release from an instrument or other object disposed therein. Distal movement of the actuation shaft 734 can also allow the first tubular portions 706A of the arms 706 to move away from one another to restore free relative rotation between the arms about the axis A1.

The actuation shaft 734 can be coupled to the clamps 708 in various ways to achieve the above functionality. For example, the actuation shaft 734 can include pins 792 slidably mounted within respective sloped slots 794 formed in the clamps 708, or vice versa. The sloped slots 794 can extend at an oblique angle relative to the axis A1. The sloped slots 794 can extend at an oblique angle relative to the axes A4. The sloped slots 794 can convert translation of the actuation shaft 734 along the axis A1 into translation of the clamps 708 along their respective axes A4. By way of further example, one of the components can include a ramped tooth that projects radially outward to contact a ramped female surface of the other component.

The actuation shaft 734 can include multiple longitudinal segments that are linked to one another such that the segments cannot translate relative to one another along the axis A1 but are free to rotate relative to one another about the axis A1. This can allow the arms 706 to rotate relative to one another about the axis A1 while allowing the clamps 708 to be rotationally fixed relative to their respective segments of the actuation shaft 734 about the axis A1. For example, the actuation shaft can include a distal segment 734d that is rotatably coupled to a proximal segment 734p as shown.

The handle assembly 702 can include one or more handle levers 716, e.g., a fixed handle lever and a movable handle lever as shown. The handle levers 716 can be configured to pivot relative to one another and to contact and bear against one another. The contact surfaces of the handle levers 716 can be shaped to provide a knee lever 796. The knee lever 796 can provide mechanical advantage, multiplying the user input force applied to the handle levers 716 to provide a relatively high locking force on the connector 700 in response to a relatively low input force. The knee lever 796 can also be self-stabilizing in the locked or fixed position, which can eliminate the need for additional locking or safety features.

In use, the arms 706 can be rotated relative to one another about the axis A1 to achieve the desired relative positioning of first and second objects disposed in the attachment features 708 of the first and second arms. The movable handle lever 716 can then be pivoted distally, pulling the actuation shaft 734 proximally to simultaneously lock (1) the attachment feature or end clamp of the first arm, (2) the attachment feature or end clamp of the second arm, and (3) the angular position of the first and second arms about the axis A1.

Figure 8A:
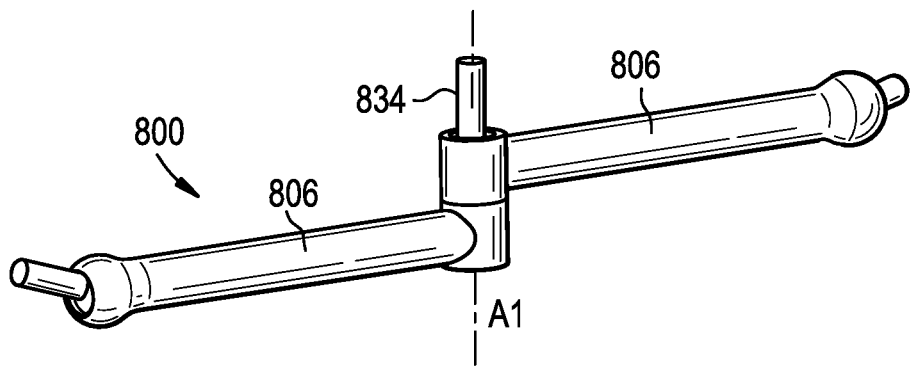
FIG. 8A is a perspective view of another connector.
Figure 8B:
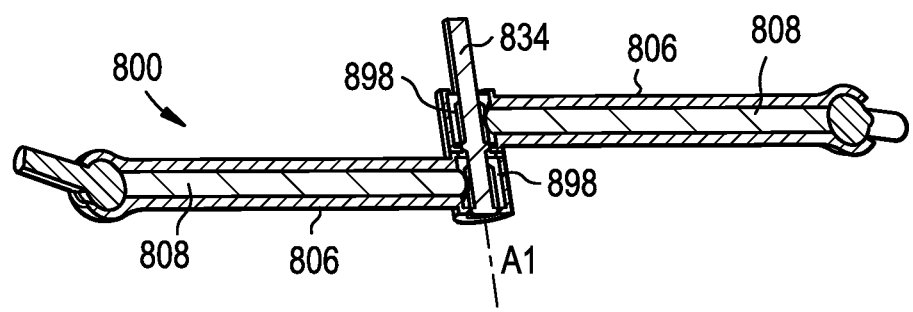
FIG. 8B is a sectional perspective view of the connector of FIG. 8A.
Figure 8C:
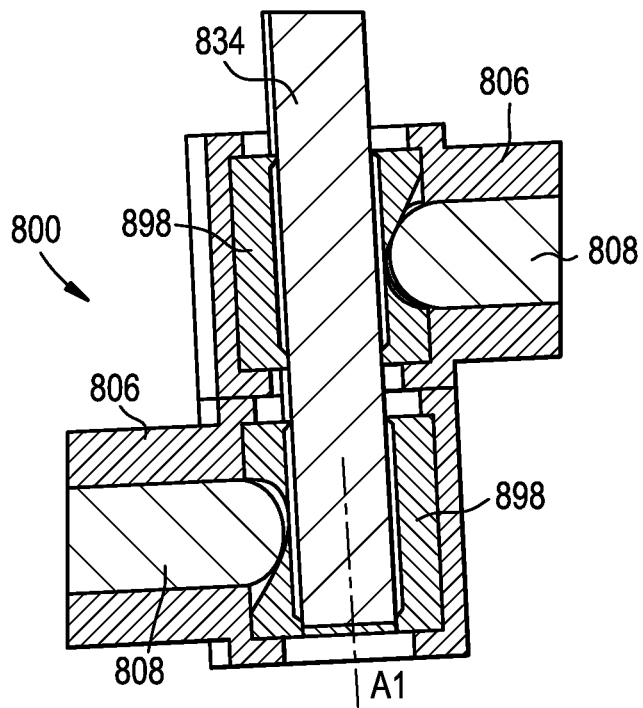
FIG. 8C is a sectional perspective detail view of the connector of FIG. 8A.

FIGS. 8A-8C illustrate another exemplary connector 800 that can be used to connect a first object to a second object. For example, the connector 800 can be used to connect first and second surgical instruments. By way of further example, the connector 800 can be used in the system 100 described above, e.g., to connect the access device 102 to the support or anchor 106. Except as indicated below and as will be readily appreciated by a person having ordinary skill in the art in view of the present disclosure, the structure and operation of the connector 800 is substantially the same as that of the connector 700 described above.

The connector 800 can include an actuation shaft 834 with ramped exterior surfaces. The ramped exterior surfaces can be formed directly on the actuation shaft 834, or on one or more bushings 898 through which the actuation shaft extends. The actuation shaft 834 can be rotatably fixed relative to the bushings 898, or can be configured to rotate relative to the bushings about the axis A1. Actuation of a handle assembly of the type described above can pull the actuation shaft 834 proximally to squeeze the bushings 898 towards one another along the axis A1. This can cause clamp rods 808 disposed in the arms 806 to be carried along ramped concave surfaces of the bushings 898, pushing the clamp rods radially outward away from the axis A1. This can urge the clamp rods 808 into firm engagement with a mating feature of an instrument or other object that is to be attached using the connector 800. For example, as shown, the clamp rods 808 can include a spherical concave surface at their free distal end that receives a convex spherical attachment feature of an instrument, and that bears against said attachment feature to lock a position and/or orientation of the instrument relative to the arm 806 when the clamp rod 808 is urged outward from the axis A1.

Figure 9A:
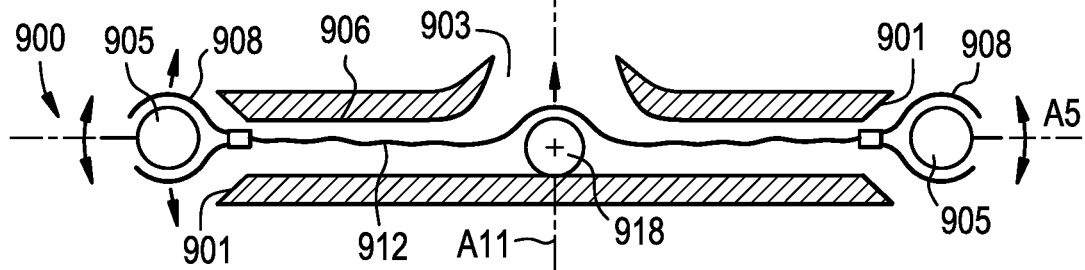
FIG. 9A is a sectional profile view of another connector, shown in an unlocked configuration.
Figure 9B:
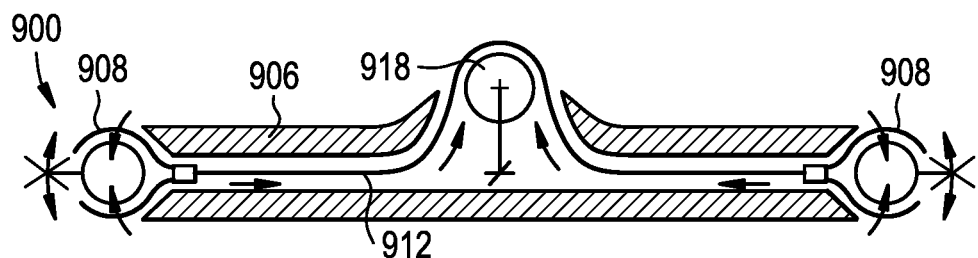
FIG. 9B is a sectional profile view of the connector of FIG. 9A, shown in a locked configuration.
Figure 9C:
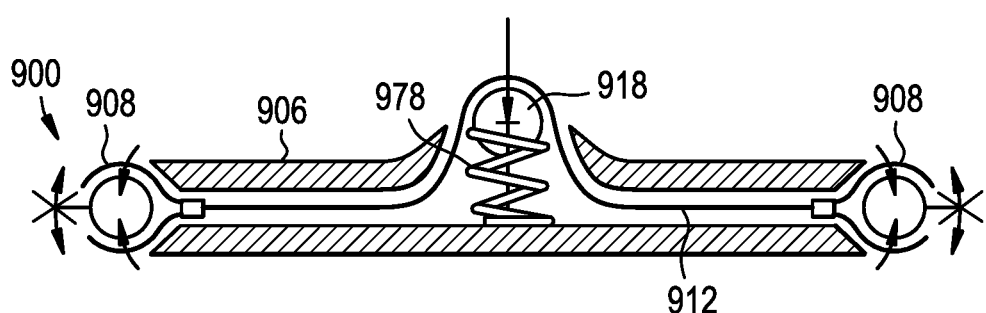
FIG. 9C is a sectional profile view of the connector of FIG. 9A, shown with a spring for biasing the connector towards the locked configuration.

FIGS. 9A-9C illustrate another exemplary connector 900 that can be used to connect a first object to a second object. For example, the connector 900 can be used to connect first and second surgical instruments. By way of further example, the connector 900 can be used in the system 100 described above, e.g., to connect the access device 102 to the support or anchor 106. Except as indicated below and as will be readily appreciated by a person having ordinary skill in the art in view of the present disclosure, the structure and operation of the connector 900 is substantially the same as that of the connector 200 described above.

The connector 900 can include a hollow rod 906 with wedged endplanes 901 and a sidewall opening 903 disposed therebetween. The rod 906 can include a central longitudinal axis A5. First and second elastic or resilient clamps 908 can be connected with a wire 912 that extends through the central lumen of the rod 906. The clamps 908 can include wedged shapes that match, or can otherwise engage with, the wedged endplanes 901 of the rod 906. The clamps 908 can include an inner shape configured to receive an attachment feature 905 of an implant, instrument, or other object therein. For example, the clamps 908 can include a spherical inner shape configured to receive a spherical instrument attachment feature 905. The wire 912 can bypass an actuation roller 918 that can be moved towards and away from the axis A5 along an axis A1 to adjust the tension in the wire 912. The connector 900 can include a handle assembly for moving the roller 918 towards or away from the axis A5. Any of the handle assemblies disclosed herein can be used.

As shown in FIG. 9B, moving the roller 918 away from the axis A5 can increase the tension applied to the wire 912. When this increased tension is applied to the cable 912, the clamps 908 can be pulled into the wedged endplanes 901 of the rod 906, thereby clamping down onto the attachment features 905 and fixing the position and/or orientation of the attachment features relative to the connector 900 and to one another.

As shown in FIG. 9C, the roller 918 can be biased away from the axis A5 by a spring 978, such that the resting position of the connector 900 is in a closed or locked state, and user input force is required to compress the spring and move the connector to the open or unlocked state.

Figure 9D:
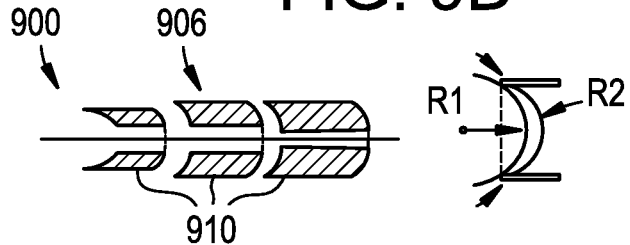
FIG. 9D is a sectional profile view of the connector of FIG. 9A, shown with a multi-segment arm.

The rod 906 can be rigid or flexible. The rod 906 can be a monolithic component or, as shown in FIG. 9D, can include a plurality of nested segments 910 as in the arm assemblies described above.

The connectors disclosed herein can be used in any of a variety of procedures, including surgical procedures of the type described herein.

For example, a first arm of the connector can be attached to a surgical access device and a second arm of the connector can be attached to a support. The surgical access device can be a cannula, a retractor, an extension tube of a bone anchor assembly, and so forth. The support can be an anatomical structure of the patient, a surgical table or an extension thereof, an implant or instrument attached to a patient (e.g., a pedicle post, a monoaxial screw head, an elongation of a monoaxial or polyaxial screw head, etc.), or various other structures. The connector can be effective to selectively maintain the access device in a fixed or substantially fixed position and/or orientation relative to the support. The connector can be unlocked to allow movement between the support and the access device in one or more degrees of freedom. The connector can be locked to prevent movement between the support and the access device in one or more degrees of freedom. The connector can rest in the unlocked state and a user input force can be required to transition the connector to the locked state. The connector can be configured to maintain itself in the locked state once positioned in the locked state, or can automatically return to the unlocked state. The connector can rest in the locked state and a user input force can be required to transition the connector to the unlocked state. The connector can be configured to maintain itself in the unlocked state once positioned in the unlocked state, or can automatically return to the locked state. The working tips of the structures that are attached using the connector can be positioned close together or far apart, with their respective positions and orientations varying as needed for a particular surgery.

Figure 10A:
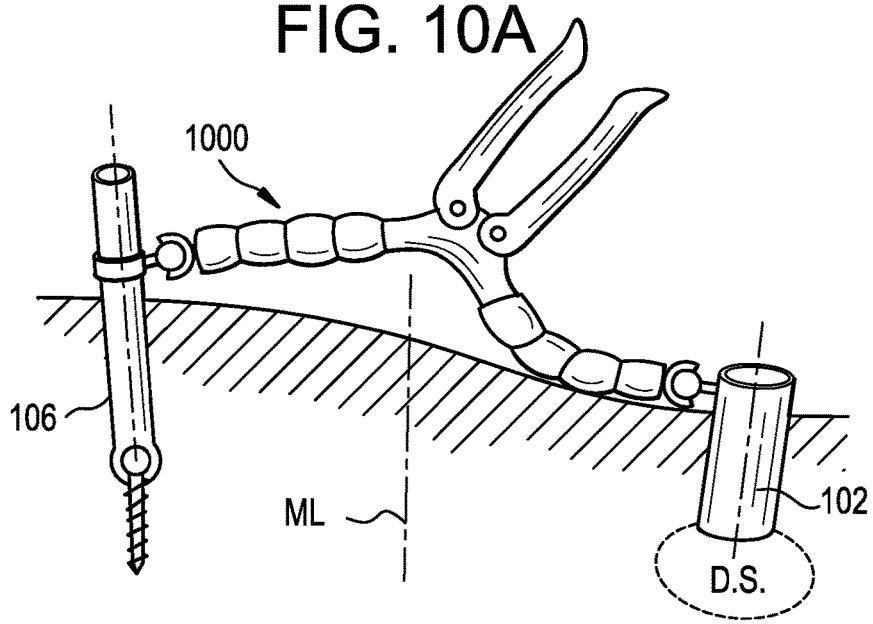
FIG. 10A is a schematic perspective view of a connector in use to connect a spinal access device to a contralateral support.

As shown in FIG. 10A, a connector 1000 of the type described herein can be used to attach a surgical access device 102 disposed on one side of a midline ML of a patient's spine to a pedicle-mounted extension post 106 disposed on an opposite, contralateral side of the midline. The surgical access device 102 can be positioned to provide access to a disc space DS of the patient's spine.

Figure 10B:
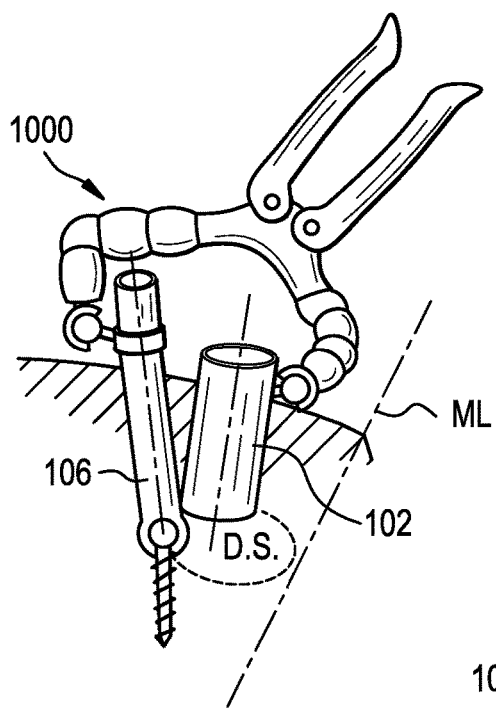
FIG. 10B is a schematic perspective view of a connector in use to connect a spinal access device to an ipsilateral support.

As shown in FIG. 10B, a connector 1000 of the type described herein can be used to attach a surgical access device 102 disposed on one side of a midline ML of a patient's spine to a pedicle-mounted extension post 106 disposed on the same, ipsilateral side of the midline. The surgical access device 102 can be positioned to provide access to a disc space DS of the patient's spine.

Use of contralateral or ipsilateral stabilization can be selected depending on the anatomical and pathologic situation. In some situations, ipsilateral support, e.g., at the same side of the patient where the surgical approach is performed, may be less invasive or provide more stability. In some situations, contralateral support may be desired, for example if a collapsed intervertebral disc leads to very narrow conditions resulting in interference between the access tube and the support if an ipsilateral arrangement is used.

Figure 10C:
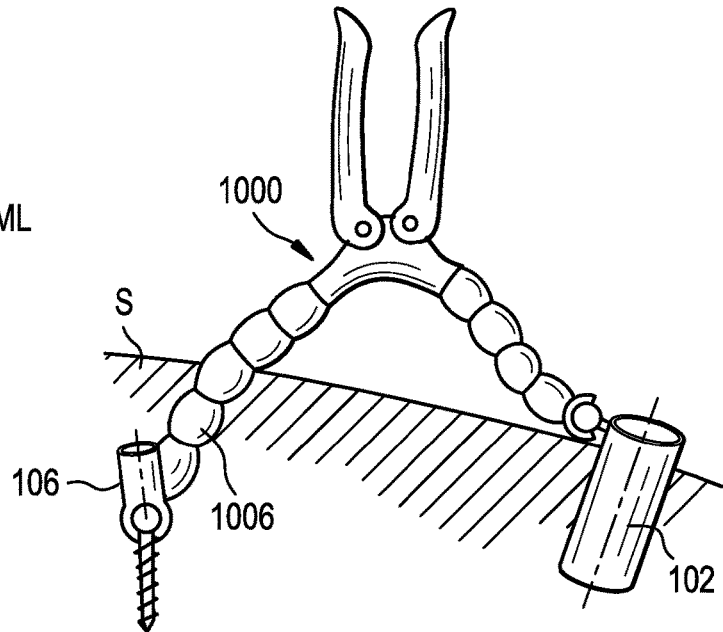
FIG. 10C is a schematic perspective view of a connector in use to connect a spinal access device to a support in which at least a portion of the connector is disposed within the patient.

When in use, the entire connector can be disposed external to the patient, e.g., as shown in FIGS. 10A-10B. Alternatively, at least a portion of the connector can be disposed internal to the patient. For example, as shown in FIG. 10C, at least a portion of one or more arms 1006 of the connector 1000 can be inserted through an incision formed in the patient's skin S to position said portion within the patient.

Connectors of the type described herein can be used in a wide array of surgical and non-surgical procedures.

Figure 10D:
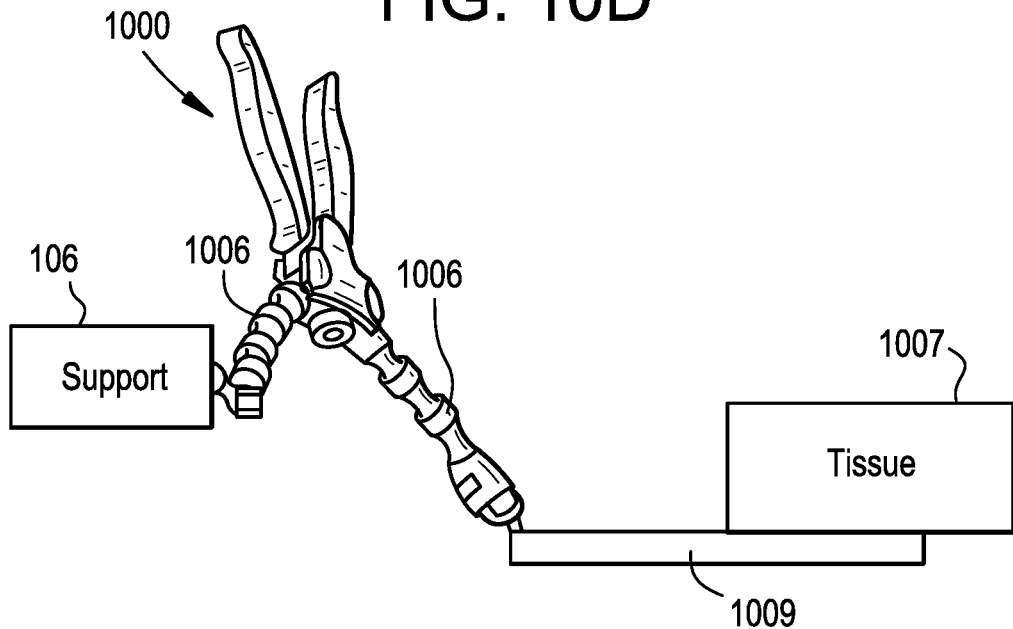
FIG. 10D is a schematic perspective view of a connector in use to support tissue.

For example, any of the connectors described herein can be used in plastic surgery. In a typical abdominoplasty procedure, the surgeon must hold or support tissue with one hand and cauterize or cut tissue with the other hand. The connector can be used to support the abdominal shelf, reducing or eliminating the need for the surgeon to support the shelf manually. As shown in FIG. 10D, one arm 1006 of the connector 1000 can be attached to a support 106, such as an operating room table. Another arm 1006 of the connector 1000 can be used to hold or support tissue 1007, either directly or by attaching the arm to a retractor, paddle, or other structure 1009 for holding or supporting tissue. The tissue can be the abdominal shelf. As the surgery progresses deeper beneath the abdominal shelf, the connector can be quickly unlocked, repositioned, and relocked to provide the tissue support desired by the surgeon.

In certain breast surgeries, an intra-mammary incision is formed and the breast is lifted to develop a pocket underneath. This can require the surgeon to hold or support tissue with one hand and cauterize or cut tissue with the other hand.

The connector can be used to support the breast, reducing or eliminating the need for the surgeon to support the breast manually. Again, as shown in FIG. 10D, one arm 1006 of the connector 1000 can be attached to a support 106, such as an operating room table. Another arm 1006 of the connector 1000 can be used to hold or support tissue 1007, either directly or by attaching the arm to a retractor, paddle, or other structure 1009 for holding or supporting tissue. The tissue can be breast tissue. As the surgery progresses, the connector can be quickly unlocked, repositioned, and relocked to provide the tissue support desired by the surgeon.

Connectors of the type described herein can reduce user strain and fatigue in any procedure in which frequent retractor positioning is required, as the connector can be quickly and easily unlocked, repositioned, and relocked.

In an exemplary procedure, one or more arms of the connector can be attached to a light source, and the connector can be used to hold the light source in a position in which it illuminates a body cavity or other surgical site.

Figure 10E:
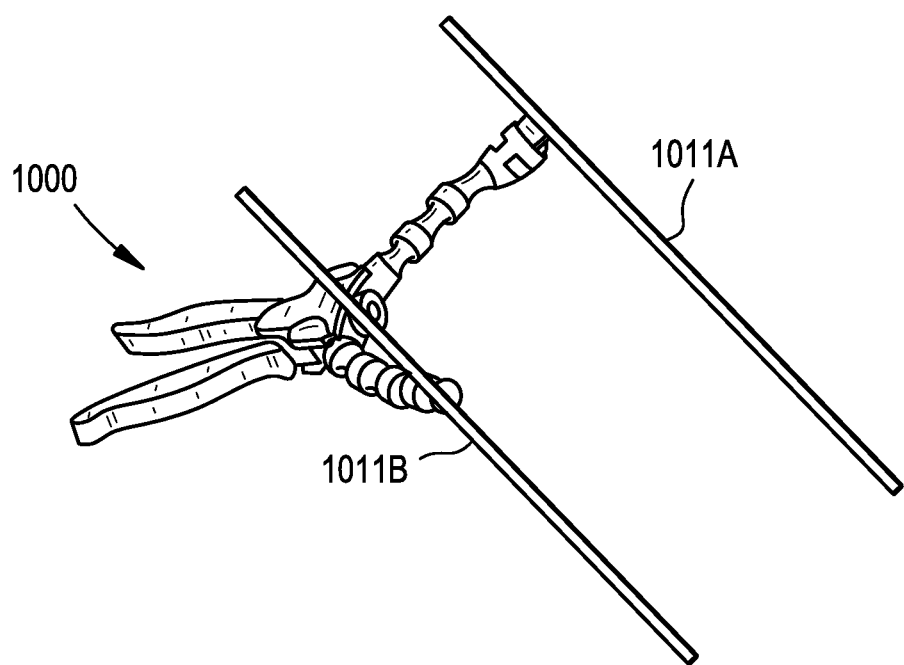
FIG. 10E is a schematic perspective view of a connector in use to automatically align two objects.

Any of the connectors described herein can be configured to automatically and consistently revert to a predetermined configuration, e.g., to automatically position first and second objects connected by the connector in a predetermined position and/or orientation with respect to one another. The connector can revert to the predetermined configuration when placed in the locked state. The geometry of the mating surfaces of the plurality of segments, and/or of the attachment features, can be selected to achieve the predetermined configuration when the connector is locked. For example, each segment can have counterpart mating surfaces that, when urged together as the wire is tensioned, cause the segments to move to a predetermined alignment. The predetermined configuration can be one in which the central longitudinal axes of two instruments 1011A, 1011B attached to the connector 1000 are placed in parallel, e.g., as shown in FIG. 10E. The instruments 1011A, 1011B can be first and second needles.

Connectors of the type described herein can be used in trans-anal surgery. For example, one arm of the connector can be coupled to a support such as an operating room table, and another arm of the connector can support an access device that is at least partially disposed in the rectum. One or more additional arms of the connector can be used to hold instruments or objects inserted through the access device, to hold a light source, or to hold any other object desired by the surgeon.

Figure 10F:
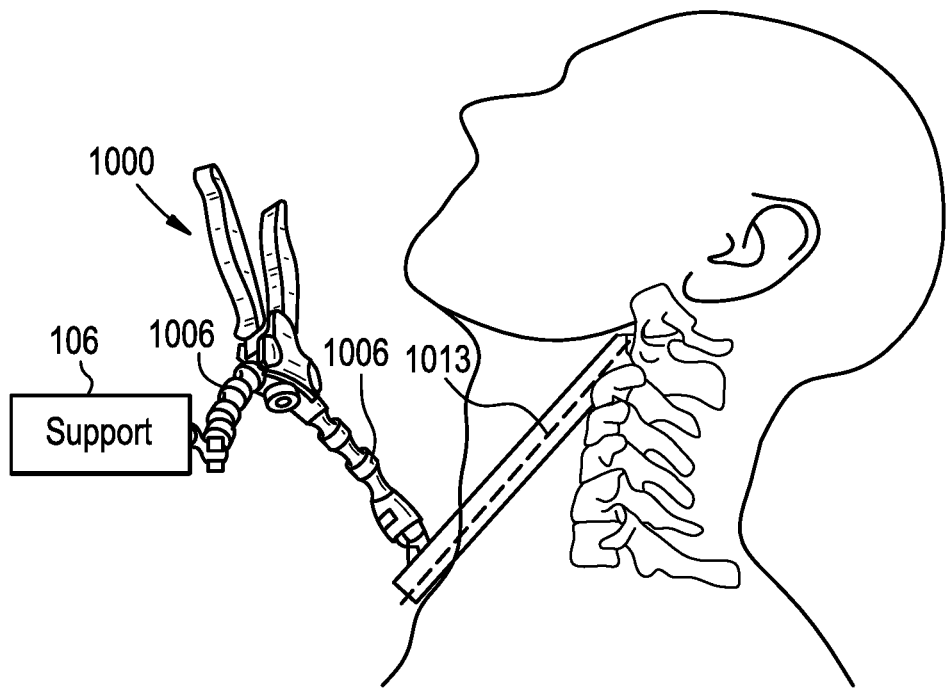
FIG. 10F is a schematic perspective view of a connector in use to support an access device for guiding placement of an odontoid screw.

Connectors of the type described herein can be used in procedures to place odontoid screws. For example, as shown in FIG. 10F, a first arm 1006 of the connector 1000 can be coupled to an access device 1013. The access device can be a cannula, retractor, drill guide, screw insertion sleeve, or the like. A second arm 1006 of the connector 1000 can be coupled to a support 106 of the type described herein, e.g., an anatomical support, pedicle screw, operating table, or the like. The connector 1000 can maintain the access device 1013 at a fixed trajectory. A lag screw, odontoid screw, or other bone anchor can be delivered through the access device 1013 to implant the bone anchor in the odontoid process, in the C2 vertebra, and/or in other bone structures, e.g., for reducing or addressing a fracture thereof.

Figure 10G:
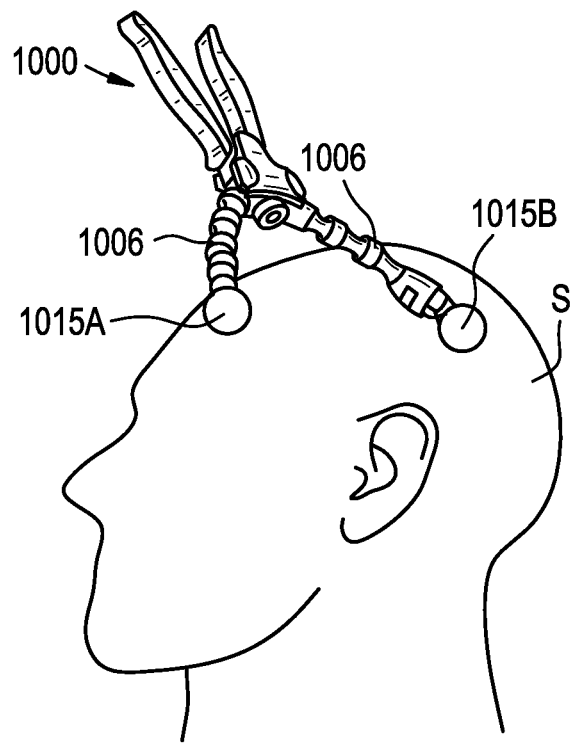
FIG. 10G is a schematic perspective view of a connector in use to connect first and second skull ports.

Connectors of the type described herein can be used to maintain access to a burr hole formed in a patient's skull. The connector can be used to maintain access to a plurality of burr holes, e.g., for evacuating epidural hematomas, subdural hematomas, hygromas, frontal bone, parietal bone, and so forth. For example, a first arm of the connector can be coupled to a retractor or skull port over a first burr hole in the patient's skull and a second arm of the connector can be coupled to a support of the type described herein, e.g., the patient's skull, the patient's skin, another retractor or port, etc. As another example, as shown in FIG. 10G, a first arm 1006 of the connector 1000 can be coupled to an access device 1015A (e.g., a cannula or skull port) over a first burr hole formed in a patient's skull S. A second arm 1006 of the connector 1000 can be coupled to an access device 1015B (e.g., a cannula or skull port) over a second burr hole. The connector can include only two arms, such that the connector is attached only to the two retractors/ports and not to an external support. As yet another example, a first arm of the connector can be coupled to a retractor or skull port over a first burr hole, a second arm of the connector can be coupled to a retractor or skull port over a second burr hole, and third arm of the connector can be coupled to a support of the type described herein.

In the examples above, the first skull port can be used to deliver material to the patient and the second skull port can be used to aspirate material from the patient. For example, saline or other flushing material can be delivered through the first port while a hematoma or other material is aspirated through the second port.

Figure 10H:
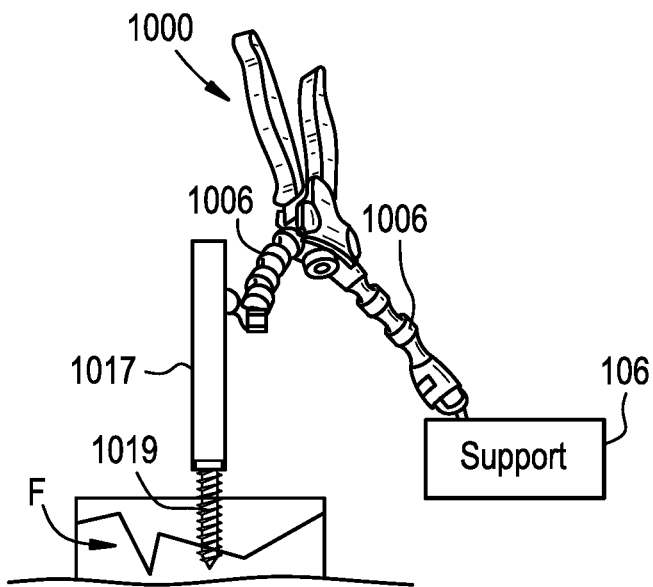
FIG. 10H is a schematic perspective view of a connector in use to support an access device for guiding a lag screw during repair of a bone fracture.

Connectors of the type described herein can be used in orthopedic or trauma surgery, for example in reducing, reconstructing, or otherwise addressing bone fractures. In an exemplary fracture repair procedure, a lag screw can be placed to reduce one or more bone fragments and hold them in a natural or desired position for healing. As shown in FIG. 10H, a first arm 1006 of the connector 1000 can be coupled to an access device 1017. The access device 1017 can be a cannula, retractor, drill guide, screw insertion sleeve, or the like. The access device 1017 can be used to guide insertion of a lag screw or nail 1019 into a bone fracture F. A second arm 1006 of the connector 1000 can be coupled to a support 106 of the type described herein, e.g., an external frame, an anatomical support, an operating table, a Jackson table, another lag screw or nail, a bone plate, or the like. The support 106 can be a lag screw or nail that has already been placed, e.g., to address the same fracture for which the current screw or nail is intended or to address a fracture proximate thereto. The support 106 can be a bone plate at least partially implanted in the patient, e.g., to address the same fracture for which the current screw or nail is intended or to address a fracture proximate thereto. The support 106 can be a bone plate through which the current screw or nail is to be placed.

The connector arm that holds the access device 1017 can be placed with intelligence. For example, the arm can be placed under robotic control, using a surgical navigation system, or using computer-assisted surgical techniques to align the access device with a predetermined insertion point and at a predetermined trajectory. The predetermined trajectory can be one in which the screw to be inserted crosses the fracture line at an optimal vector for reducing the fracture. As another example, intelligence can exist between multiple arms of the connector. The connector arms can be equipped with MEMS sensors, navigation beacons, or other components to determine their relative position and/or orientation. The access device can be placed using preoperative or intraoperative planning. The access device can be placed using 3D surgical navigation, ultrasound, fluoroscopy, etc. The access device can be coupled to an electronic display that shows a virtual reality (VR) and/or augmented reality (AR) image of the fracture line and alignment of the access device with the fracture line. The user can then manipulate the connector until the desired alignment is reached, e.g., as confirmed via the display, lock the connector in place, and then insert the screw or nail.

Connectors of the type described herein can be used in tibial plateau fracture reduction. One arm of the connector can attach to a tibial bone plate and another arm of the connector can attach to and align a working channel, guide sleeve, or other access device over the opening of the plate through which a screw is to be inserted. Connectors of the type described herein can be used in navicular or scaphoid fracture reduction. Connectors of the type described herein can be used for mid-shaft fractures with multiple butterfly fragments.

When used in applying a fixation construct to a patient, connectors of the type described herein can be attached to part of the final fixation construct, e.g., when adding a screw or bone anchor in or around the construct.

Figure 10I:
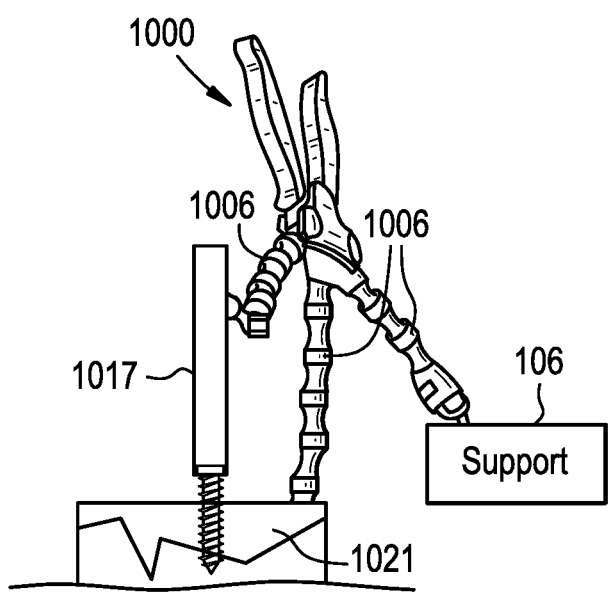
FIG. 10I is a schematic perspective view of a connector in use to support an access device and a bone fragment during repair of a bone fracture.

Connectors of the type described herein can be used to hold a bone fragment in place while inserting a screw or nail to repair a fracture. For example, as shown in FIG. 10I, one arm 1006 of the connector 1000 can be used to hold a bone fragment 1021, one arm 1006 can be used to hold an access device 1017, and one arm 1006 can be attached to a support 106. As another example, one arm of the connector can be used to hold an access device, which in turn can be used to hold a bone fragment in place, and another arm of the connector can be attached to a support. The access device can be shaped to facilitate bone retention, for example by having a distal end that is concave, convex, a negative of the bone surface, coated with an adhesive, or that includes teeth or other gripping features for holding the bone fragment in place. An exemplary method of treating a bone fracture can include: unlocking the connector; attaching a bone fragment to an arm of the connector; positioning the fragment in a desired location; aligning a guide channel attached to another arm of the connector with a fracture plane, screw insertion point, or other location; locking the connector; and inserting a screw or nail through the guide channel to secure the fragment in the desired location.

Use of a connector of the type described herein in fracture repair procedures can provide advantages over existing techniques that largely rely on eyeballing, freehand approximation, or extensive use of fluoroscopy.

Figure 10J:
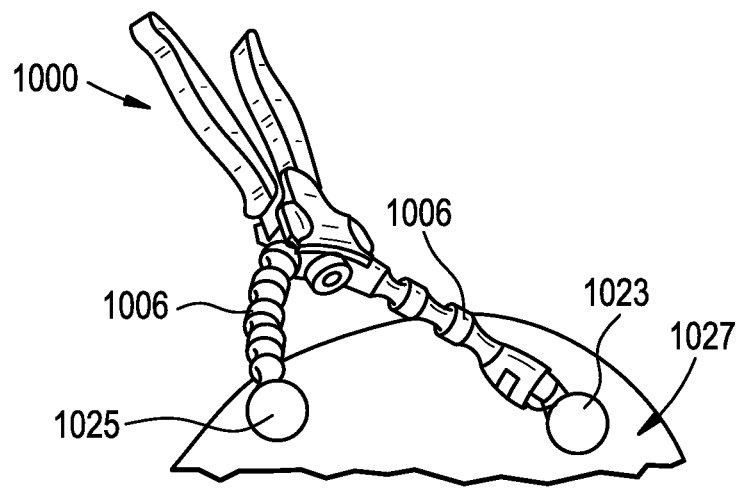
FIG. 10J is a schematic perspective view of a connector in use to maintain a position between a visualization device and a surgical instrument.

Connectors of the type described herein can be used in minimally-invasive surgery. For example, a connector can be used to maintain alignment between a scope or visualization device and a surgical instrument. In arthroscopic joint surgery, e.g., of the knee, an arthroscope can be inserted through a first skin portal and a surgical instrument, e.g., for cutting, shaving, or manipulating tissue, can be inserted through a second skin portal. Typically, the user wishes to align the field of view of the arthroscope with the distal end or working portion of the instrument. If the user turns away momentarily to attend to other surgical tasks, the arthroscope and/or the instrument can move, causing the user to lose visualization of the instrument. The user must then go through the cumbersome task of realigning the arthroscope with the instrument to restore visualization. This can be avoided using connectors of the type herein. For example, as shown in FIG. 10J, one arm 1006 of a connector 1000 can be attached to an arthroscope or other visualization device 1023. The visualization device can be inserted through a first skin portal. The visualization device can be inserted into a joint of a patient, e.g., into a knee joint 1027 as shown. Another arm 1006 of the connector 1000 can be attached to a surgical instrument 1025, or to a guide sleeve or access device through which a surgical instrument is inserted into the patient. The guide sleeve can be inserted through a second skin portal that is discrete from the first skin portal. The connector 1000 can be locked to maintain a fixed position and/or orientation between the guide sleeve or instrument 1025 and the visualization device 1023. For example, the arms of the connector can be locked such that the distal ends of two objects held thereby are focused on the same area or substantially the same area. Accordingly, the user can release one or both objects and attend to other tasks without losing visualization of the instrument.

Figure 10K:
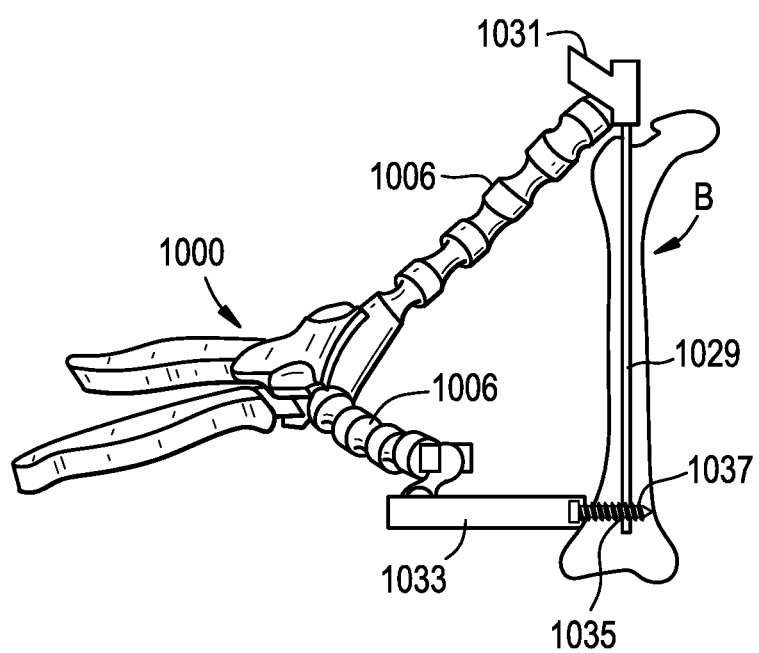
FIG. 10K is a schematic perspective view of a connector in use to support an access device for guiding placement of a locking screw in an intramedullary device.

Connectors of the type described herein can be used in placement of intramedullary (IM) devices, rods, or nails, e.g., to treat long bone fractures. For example, a connector can be used to align a locking screw with a locking hole formed in the IM device. As shown in FIG. 10K, one arm 1006 of a connector 1000 can be attached to the IM rod 1029 or to an IM rod inserter 1031 mounted thereto while the rod 1029 is inserted into a bone B. Another arm 1006 of the connector 1000 can be attached to an access device 1033. The access device 1033 can be a cannula, retractor, drill guide, screw insertion sleeve, or the like. The arms 1006 of the connector 1000 can be manipulated to align the access device 1033 with a locking hole 1035 of the IM rod 1029. The connector 1000 can then be locked in position and the access device 1033 can be used to guide drilling of the bone B and subsequent insertion of a locking screw 1037 through the locking hole 1035 of the IM rod 1029. Use of the connector to maintain the access device at a fixed position and/or orientation relative to the IM rod can reduce or eliminate the need for fluoroscopy to confirm that the access device has not drifted. For example, the user can switch from a drill to a screw driver without having to re-check the position of the cannula under fluoroscopy, potentially reducing radiation exposure to the patient. Instead of attaching the connector to the IM rod or inserter, or in addition thereto, one arm of the connector can be clamped or otherwise attached to bone, or can be attached to a support of the type described herein.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A connector, comprising:
   a plurality of arms each having a plurality of nested segments and an attachment feature for attaching an instrument to the arm; and
   a handle, wherein the handle is movable between a first position in which the plurality of nested segments of each of the plurality of arms are movable relative to one another and a second position in which the plurality of nested segments of each of the plurality of arms are fixed relative to one another;
   wherein movement of the handle to the second position is effective to lock the attachment feature of at least one of the plurality of arms.

2. The connector of claim 1, wherein the plurality of arms comprises first and second arms having respective first and second attachment features, wherein the attachment features are movable in one or more degrees of freedom relative to one another when the handle is in the first position, and wherein said one or more degrees of freedom are locked when the handle is in the second position.

3. The connector of claim 2, wherein:
   movement of the handle to the second position is effective to lock movement of the first arm, lock movement of the second arm, lock the first attachment feature to a first instrument, and lock the second attachment feature to a second instrument; and
   movement of the handle to the first position is effective to restore movement of the first arm, restore movement of the second arm, unlock the first attachment feature from the first instrument, and unlock the second attachment feature from the second instrument.

4. The connector of claim 1, further comprising an actuation wire extending through the plurality of nested segments, wherein the handle in the second position increases tension on the actuation wire to fix the segments and wherein the handle in the first position decreases tension on the actuation wire to allow movement between the segments.

5. The connector of claim 4, wherein the actuation wire is coupled to the attachment feature such that increasing tension on the actuation wire closes the attachment feature.

6. The connector of claim 4, wherein the handle includes a wire track in which a portion of the actuation wire is disposed, the wire track being open to an exterior side surface of the handle to allow the wire to be introduced laterally into the wire track.

7. The connector of claim 4, wherein the handle includes a bearing element engaged with the actuation wire.

8. The connector of claim 7, wherein movement of the handle causes translation of the bearing element along a tension axis, thereby increasing or decreasing tension applied to the actuation wire.

9. The connector of claim 7, wherein the handle includes first and second branches, each being operatively associated with an arm of the connector, the branches defining a cavity therebetween.

10. The connector of claim 9, wherein the bearing element is mounted on a plate slidably disposed in the cavity.

11. The connector of claim 10, wherein opposed edges of the plate are slidably disposed within corresponding tracks formed in the branches.

12. The connector of claim 1, further comprising an actuation shaft disposed within a lumen of the handle.

13. The connector of claim 12, further comprising a linkage bar coupled to a movable handle lever of the handle and to the actuation shaft.

14. The connector of claim 13, further comprising an adjustment knob threadably mated to the actuation shaft to form an assembly, wherein rotation of the adjustment knob adjusts the length of the assembly as measured along a tension axis, thereby adjusting the amount of tension applied to an actuation wire of the at least one arm when the handle is moved between the first and second positions.

15. The connector of claim 1, further comprising a locking mechanism for selectively maintaining the handle in at least one of the first and second positions.

16. The connector of claim 15, wherein the locking mechanism comprises a movable handle lever pivotally coupled to a linkage bar and configured to enter an over-center condition when the handle is in the second position.

17. The connector of claim 1, wherein the plurality of nested segments can pitch, yaw, and roll relative to one another when the handle is in the first position.

18. The connector of claim 1, wherein the attachment feature defines a central opening through which an instrument or other object can be received.

19. The connector of claim 1, wherein the attachment feature applies a pre-load or provisional friction fit to an object received therein when the handle is in the first position.

20. The connector of claim 1, wherein the attachment feature comprises at least one of a ring clamp, a lasso, an end-loading jaw, a side-loading jaw, and a spherical clamp.

21. The connector of claim 1, wherein the handle is biased towards the second position.

22. The connector of claim 21, wherein the connector includes a spring element that biases the handle towards the second position, wherein the spring element urges an actuation wire extending through the at least one arm in a proximal direction to apply tension thereto.

23. The connector of claim 22, wherein moving the handle to the first position compresses the spring element to reduce tension applied to the actuation wire.

24. The connector of claim 22, wherein the handle includes a scissor linkage that expands to compress the spring element when the handle is in the first position.

25. The connector of claim 1, wherein the plurality of arms comprises first and second arms, and wherein the handle includes a fixed handle lever, a first movable handle lever movable with respect to the fixed handle lever to lock the first arm, and a second movable handle lever movable with respect to the fixed handle lever to lock the second arm.

26. The connector of claim 1, wherein the at least one arm of the plurality of arms is configured to be coupled to a support.

27. The connector of claim 26, wherein the support is an anatomical structure of a patient.

28. The connector of claim 26, wherein the support is a body of a patient.

29. The connector of claim 26, wherein the support is skin of a patient.

30. A connector, comprising:
    at least one arm and an attachment feature for attaching an instrument to the arm; and
    a handle, wherein the handle is movable between a first position in which the attachment feature is movable relative to the instrument and a second position in which the attachment feature is fixed relative to the instrument;

wherein the at least one arm is configured to connect the instrument to an anatomical structure of a patient, wherein the at least one arm extends between the handle and the attachment feature, and wherein movement of the handle to the second position is effective to lock the attachment feature to the instrument.

31. The connector of claim 30, wherein the anatomical structure is a body of a patient.

32. The connector of claim 30, wherein the anatomical structure is skin of a patient.

33. The connector of claim 30, wherein the at least one arm comprises first and second arms, and wherein the first arm is coupled to the instrument and the second arm is coupled to the anatomical structure.

34. A connector, comprising:

at least one arm having a plurality of nested segments and an attachment feature for attaching an instrument to the arm; and a handle movable between a first position in which the plurality of nested segments are movable relative to one another and a second position in which the plurality of nested segments are fixed relative to one another;

wherein the at least one arm is configured to connect the instrument to an anatomical structure of a patient, wherein the at least one arm extends between the handle and the attachment feature, and wherein movement of the handle to the second position is effective to lock the attachment feature.

* * * * *